(12) United States Patent
Rozier et al.

(10) Patent No.: US 8,006,699 B2
(45) Date of Patent: Aug. 30, 2011

(54) SITE GUARD FOR INTRAVENOUS SITES AND OTHER SENSITIVE AREAS

(76) Inventors: Betty M. Rozier, Hazelwood, MO (US); Lisa M. Vallino, Hazelwood, MO (US)

( * ) Notice: Subject to any disclaimer, the term of this patent is extended or adjusted under 35 U.S.C. 154(b) by 322 days.

(21) Appl. No.: 10/501,604

(22) PCT Filed: Jan. 16, 2003

(86) PCT No.: PCT/US03/01216
§ 371 (c)(1),
(2), (4) Date: Oct. 28, 2004

(87) PCT Pub. No.: WO03/059154
PCT Pub. Date: Jul. 24, 2003

(65) Prior Publication Data
US 2005/0076921 A1    Apr. 14, 2005

Related U.S. Application Data

(63) Continuation-in-part of application No. 10/046,800, filed on Jan. 15, 2002, now abandoned, which is a continuation-in-part of application No. 09/608,648, filed on Jun. 30, 2000.

(60) Provisional application No. 60/349,828, filed on Jan. 16, 2002, provisional application No. 60/261,892, filed on Jan. 16, 2001.

(51) Int. Cl.
| | |
|---|---|
| *A61F 13/00* | (2006.01) |
| *A61F 5/37* | (2006.01) |
| *A61B 19/00* | (2006.01) |
| *A61M 31/00* | (2006.01) |
| *A61M 5/32* | (2006.01) |

(52) U.S. Cl. ........ 128/878; 128/846; 128/869; 128/877; 128/879; 128/888; 604/48; 604/174; 604/179; 604/180

(58) Field of Classification Search .................. 128/846, 128/877–879, 888–889; 604/174; 33/512; 2/169; 602/21
See application file for complete search history.

(56) References Cited

U.S. PATENT DOCUMENTS

| | | | |
|---|---|---|---|
| 3,176,686 A | 4/1965 | Barnes | |
| 3,194,235 A * | 7/1965 | Cooke | 128/888 |
| 4,870,976 A | 10/1989 | Denny | |
| 5,167,240 A * | 12/1992 | Rozier et al. | 128/888 |
| 5,238,010 A * | 8/1993 | Grabenkort et al. | 128/888 |
| 5,577,516 A * | 11/1996 | Schaeffer | 128/877 |
| 5,722,959 A * | 3/1998 | Bierman | 604/174 |
| 5,807,300 A * | 9/1998 | Nix, Jr. | 602/79 |
| 6,113,577 A | 9/2000 | Hakky et al. | |
| 6,132,399 A * | 10/2000 | Shultz | 604/174 |
| 6,142,966 A * | 11/2000 | Hely | 602/64 |
| 6,257,240 B1 * | 7/2001 | Shesol | 128/877 |
| 6,322,539 B1 * | 11/2001 | Cook | 604/174 |
| 6,526,981 B1 * | 3/2003 | Rozier et al. | 128/846 |

* cited by examiner

*Primary Examiner* — Patricia M Bianco
*Assistant Examiner* — Brandon Jackson
(74) *Attorney, Agent, or Firm* — Mayer Brown LLP

(57) ABSTRACT

A multipurpose site guard for use at all peripheral and central venipuncture infusion sites, sensitive areas, and for pediatric and adult patients. The guard is a hollow plastic member with a base and a sidewall curved upwardly and inwardly to form a cover which is form fitted to the infusion site under finger pressure and which can be taped in place. Improvements to this invention include holding the guard in place with a fabric connector having closure means and cushioning the guard's base with a soft material.

30 Claims, 23 Drawing Sheets

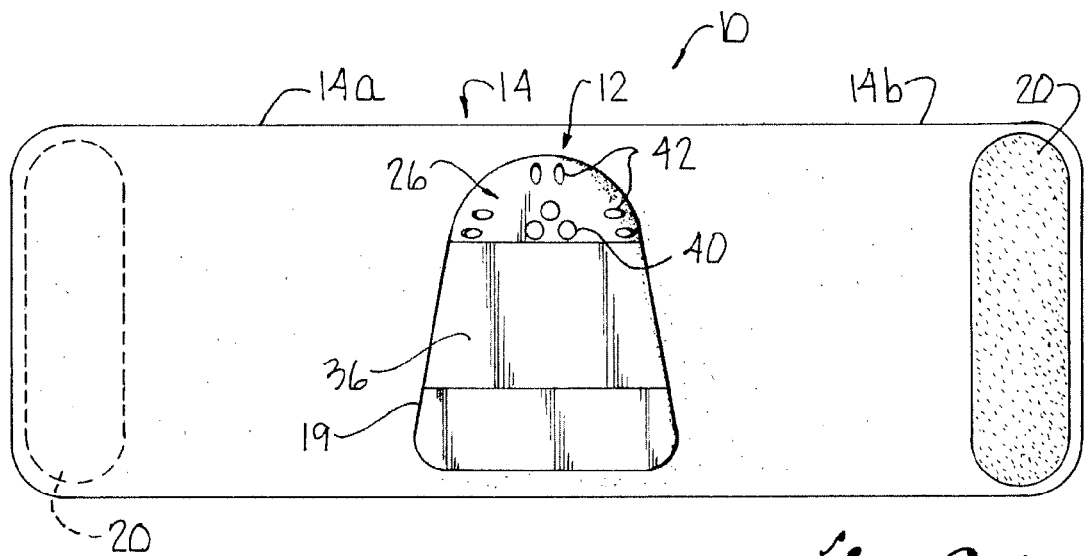
fig. 3a.
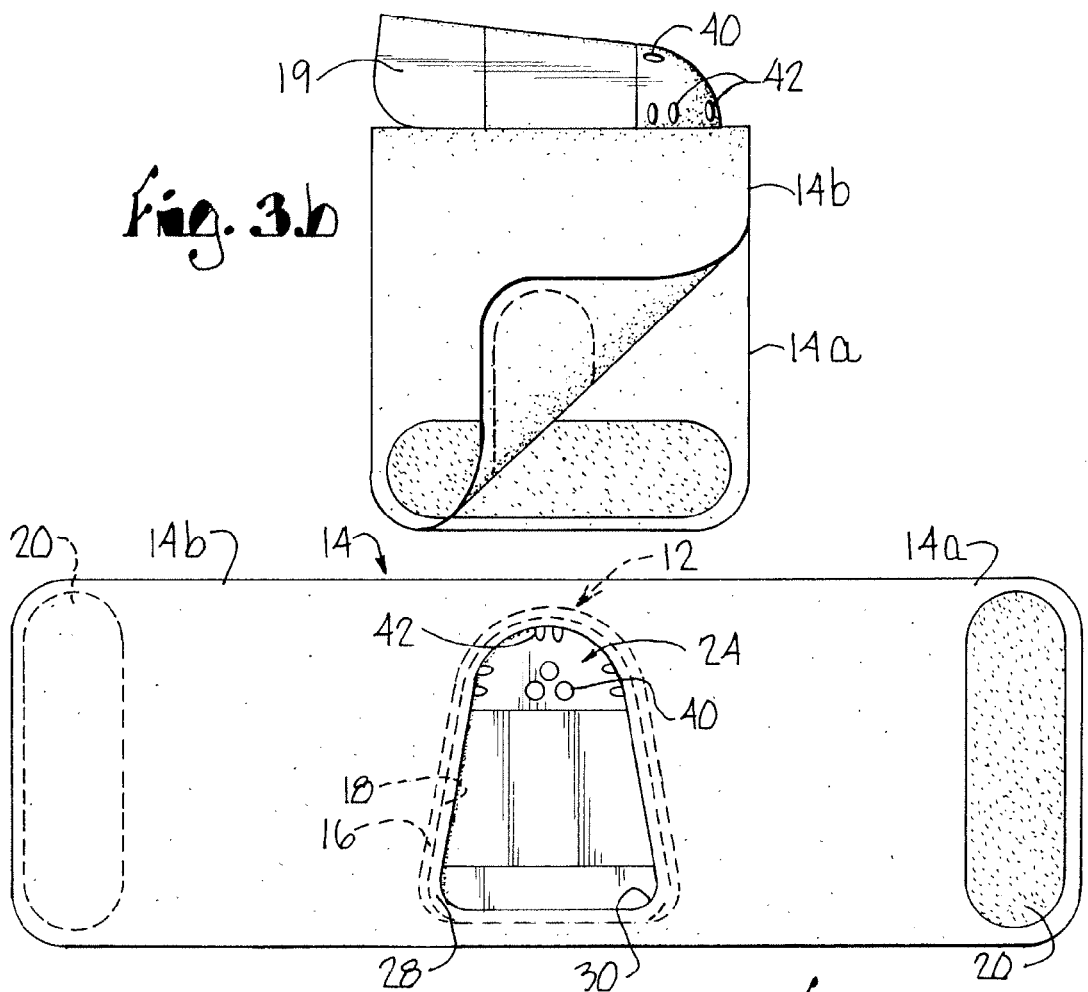
fig. 3b
fig. 3c

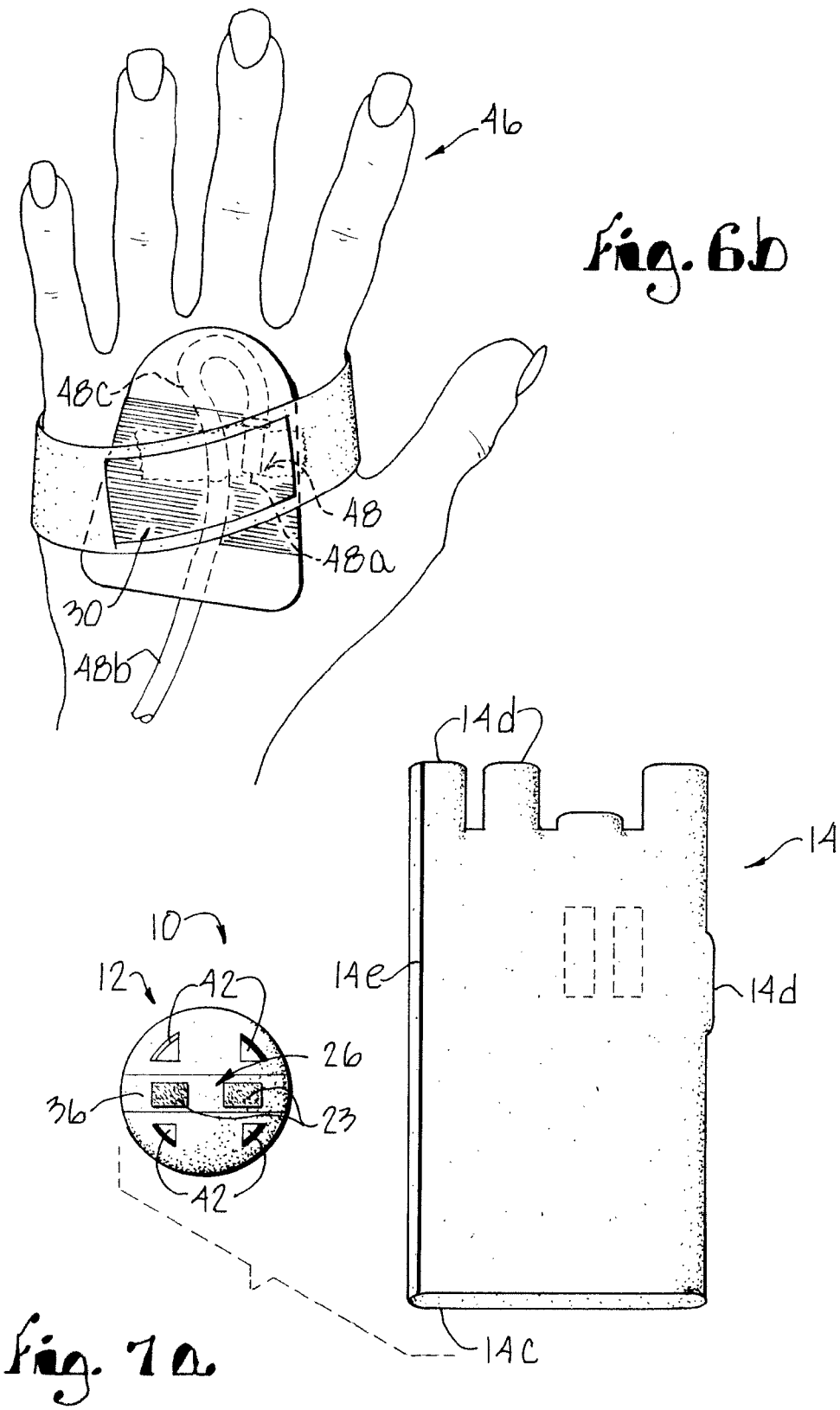

SITE GUARD FOR INTRAVENOUS SITES AND OTHER SENSITIVE AREAS

RELATED APPLICATION DATA

This application (1) claims priority to U.S. Provisional patent application No. 60/349,828, filed Jan. 16, 2002, and (2) is a continuation-in-part application of U.S. patent application Ser. No. 10/046,800, filed Jan. 15, 2002 now abandoned, which is a continuation-in-part application of U.S. patent application Ser. No. 09/608,648, filed Jun. 30, 2000, and claims priority to U.S. provisional application no. 60/261,892, filed Jan. 16, 2001 and to PCT/US01/2088, filed Jun. 30, 2001, the entire disclosures of which are incorporated herein by reference.

FIELD OF INVENTION

The present invention relates to a guard for protecting sites on the body, including a fabric connector with closure means that holds the guard in place without applying adhesive to a patient's body.

BACKGROUND OF INVENTION

Parenteral administration of therapy is a common and often life-saving medical technique. Perhaps its most common form is peripheral intravenous (IV) infusion, a high volume, high risk, high cost therapy that affects virtually all patient populations in all healthcare settings. In this procedure, a needle breaks a patient's skin and enters a vein, and additional equipment delivers therapeutic infusates such as antibiotics, hydration fluids, hyperalimentation, pain management drugs, chemotherapy drugs, indigestible drugs, or blood products into the body. Similar equipment may drain harmful fluids away from the body, such as fluids accumulating around infected wounds or emptying into colostomy bags. Patients may receive IV or other parenteral therapy for a few hours, a few days, a few weeks, a few months, or even years.

On the human body, there are a number of possible venipuncture sites. The scalp, upper extremity and lower extremity contain many peripheral venipuncture sites; the basilic vein in the antecubital area is the best vein for placement of midline catheters, another type of peripheral venous access device that can tolerate longer dwell times, while central venipuncture sites may access the superior vena cava.

The major superficial veins of the scalp are the frontal, superficial temporal, posterior auricular, supraorbital, occipital and posterior facial. In the upper extremity, venipuncture sites include the cephalic, median basilic and median antecubital veins, as well as the dorsal venous arch. The saphenous veins, the median marginal veins and the veins of the dorsal arch of the lower extremities are also used.

Central venous access is achieved when the catheter tip of the access device is located in the lower one-third of the superior vena cava close to its junction with the right atrium of the heart. Central venipuncture sites include the external jugular, the internal jugular or the subclavian vein. The inferior vena cava is entered through the femoral vein. Central access to the superior vena cava is commonly achieved through peripherally inserted central catheters known as PICC lines, which are inserted in the antecubital area into the basilic vein and may take the place of multiple repeated peripheral IVs.

The selection of an IV site depends on a host of considerations including the age of the patient, condition of the patient, what kind of fluid is to be infused, rate at which the fluid is to be infused and so forth. In general, if the patient is an adult, the best venipuncture sites, in order of preference, are the lower arm and hand, the upper arm, and the antecubital fossa. If the patient is an infant, a scalp vein may be used because it is accessible and when other peripheral attempts have failed.

Needles and catheters of various sorts are used for IV infusions. In the past, the same needle used to puncture the vein was also used for infusing the fluid. Present practice, however, is to infuse the fluid through a catheter that is planted with a needle which is then withdrawn. Currently there are two major types of catheters—namely, over-the-needle catheters and through-the-needle catheters. A third type, steel butterfly needles, formerly used in treating children, have been superseded by over-the-needle catheters.

Old fashioned needles and modern catheters terminate in a hub for connection to a fluid supply line by means of a separable tapered part. The friction joint between the hub and the supply line sometimes becomes detached even with a threaded locking connector such as a luer lock. When this happens, fluid is lost and the patient may be seriously affected beyond the value of the fluid lost. Needles and catheters are also subject to inadvertent displacement whereby the needle or catheter is withdrawn from the vein or perforates the vein's opposite wall causing the infused fluid to infiltrate and swell the surrounding tissue. This thwarts infusion therapy and causes other problems. Displacement of the needle or catheter is particularly likely when the venipuncture infusion site is adjacent a joint.

Agencies such as the Center for Disease Control require that catheters be changed every 48 hours if an institution has an incidence of phlebitis greater than 5%, and every 72 hours if the incidence of phlebitis is less than 5%. However, such agencies seek to extend catheter dwell time to 96 hours. Prolonging the lifespan of peripheral catheters benefits patients by decreasing the number of IV starts, decreasing infection due to fewer needlesticks, decreasing the incidence of thrombus, decreasing the cost of IV start supplies, decreasing nursing time and physiologic cost to the patient, and in some cases, fewer interruptions in nutritional therapy. Also, increasing the dwell time can salvage more veins for use at a later date.

The simplest way to stabilize the joint between the hub and the supply line and to prevent the needle and catheter from being displaced is with adhesive tape (after application of a transparent dressing that maintains sterility). The supply line tubing is taped to the patient over the transparent dressing and "looped," or directed, back to its source. This loop needs to be secure to prevent mechanical catheter manipulation, so that the needle or catheter is less likely to become dislodged if the tubing is accidentally bumped or pulled. If the venipuncture site is adjacent a joint, the joint is often immobilized.

If the IV equipment is taped but otherwise unguarded, the catheter may still be accidentally dislodged or, in the case of adult patients with impaired senses or involuntary movement and pediatric patients, pulled out by the patient or one of his caregivers or visitors. A taped but otherwise uncovered infusion site may frighten pediatric patients and be a stressor even to adults, particularly if they are very old or sick.

In addition to tape, devices have been proposed for guarding the needle or catheter at the infusion site and for protecting the joint between the needle or catheter and the supply line. Many of these devices are specially designed for use at a particular infusion site and are big, expensive and mechanically complicated. For example, there are devices with domes over the infusion site and with means for immobilizing the elbow joint for intravenous infusion adjacent the joint of an adult. There are other special purpose devices for protecting the infusion site on a child's scalp and so forth.

The applicants' U.S. Pat. No. 5,167,240 and Des. 335,926 teach a hollow member to cover puncture sites made by IV needles (the "I.V. HOUSE"®). Through principles of blow dispersion and absorption, the I.V. HOUSE helps protect sites such as injection sites which are a catheter length away from the infusion sites, as well as venipunctures and their accompanying IV needles and catheters from being bumped or pulled. The I.V. HOUSE is used in the health care industry on adult and pediatric patients.

Hollow members are usually secured in place by adhesives such as tape. However, the use of adhesives is problematic for many patients as epidermal stripping may occur. Patients may have external or subsurface conditions adjacent a site that may be irritated or exacerbated by the adhesive's chemicals, by the tape's nonporous nature, or by the mechanical pulling needed to remove the tape. Some patients are immunocompromised or sensitive or allergic to the adhesive, or become so during the course of treatment. The skin of geriatric and pediatric patients, especially neonates, tends to be sensitive even when healthy. Other patients have unhealthy skin, such as patients suffering from diseases of or affecting the skin including but not limited to Stevens-Johnson syndrome, skin cancer, acne, allergic rashes or general dermatitis, and may also be harmed by the use of adhesives. The sensitivity of patients' skin with burns, for example from fire, the sun, contact with chemicals or chemotherapy treatments, presents enormous difficulties in protecting IV puncture sites and other surface or subsurface problems. Many patients have varying concentrations of hair on their skin, making tape painful to remove unless the site is clipped with scissors. Patients with these or other skin conditions may suffer mild to severe itching, rashes, blisters, open sores, sloughing of the skin, even scars, among other things, from the use of adhesives on their skin. In the worst case, removal of the tape can cause epidermal stripping, removal of a layer of skin, when the adhesive is removed in patients with fragile skin.

Using tape to secure hollow members has other difficulties. When the environment or the patient's skin becomes moist, for instance in humid climates or patients who perspire profusely, adhesives may loosen and thus lose their supportive value. Tape does not adhere well to raw, burned, or otherwise unhealthy skin, or to sites in irregular places such as the head. Adhesives also loosen if they are moved too much, or if they do not have a solid flush surface to stick to. Furthermore, tape can stick to a health care provider's glove and tear it, potentially exposing the worker to bloodborne pathogens and compounding concerns about introducing new infections to a patient.

In view of the above, there is a continuing need for a general-purpose guard for a variety of sites on pediatric and adult patients. However, the use of tape to secure a hollow member over one or more sites creates problems in a variety of patients. The present invention seeks to allay that problem.

SUMMARY OF INVENTION

The site guard of the present invention avoids difficulties with adhesives by securing a protective hollow member to one or more desired sites with a fabric connector that does not use adhesives on patients' skin. Besides protecting patients from exposure to adhesives, the inventive site guard's universal design and use is more adaptable to irregular or hirsute body surfaces than those secured to patients' skin with adhesives. The site guard adapts well to humid environments and allows for better stabilization of IV sites in cases where tape is inadequate or painful, such as on the sensitive skin of geriatric patients and on neonatal and other pediatric patients, and when patients' skin is otherwise moist, sensitive or unhealthy. Overall, the use of a fabric connector to secure a hollow member over a site helps maintain the integrity of healthy and unhealthy skin and reduces irritation caused by tape in contact with skin or device in contact with skin.

The site guard of the present invention comprises a hollow member affixed to a fabric connector. The hollow member has a base with an edge to be positioned upon a patient adjacent a site, dimensioned so as to completely cover the site. The fabric connector is removably or permanently affixed to the hollow member to hold the site guard in place over the site. The present invention also includes a method for protecting a site, comprising placing a hollow member over the site and securing it to a patient with a fabric connector having closure means that avoids applying adhesive to the patient's skin.

The site guard's easy-to-fasten fabric connector benefits at-home patients; in some embodiments, the entire apparatus may be removed, washed and reused. It also improves stability over tape in active patients apt to dislodge their IV inserts, such as active children, epileptic, patients with involuntary movements, delirious or physically aggressive patients, or patients who are simply out of bed and ambulatory.

BRIEF DESCRIPTION OF THE FIGURES

The accompanying drawings illustrate various embodiments of the contemplated invention. Corresponding reference characters refer to corresponding parts throughout the several views of the drawings, and in which:

FIG. 3a is plan view of the top of the site guard of the present invention, with the fabric connector affixed to the lower edge and inner sidewall of the hollow member.

FIG. 3b is a perspective view of the site guard of the present invention.

FIG. 3c is a plan view of the bottom of the site guard of the present invention.

FIG. 6b is a plan view of the site guard of the present invention, completely assembled.

FIG. 7a is a plan view of the site guard of the present invention, where the tubular mesh fabric connector is completely separate from the hollow member.

FIG. 18a is a top plan view of an embodiment of the hollow member including a member flange.

FIG. 18b is a right side view of the embodiment of the site guard shown in FIG. 18a.

DETAILED DESCRIPTION OF THE INVENTION

Figure 1A:
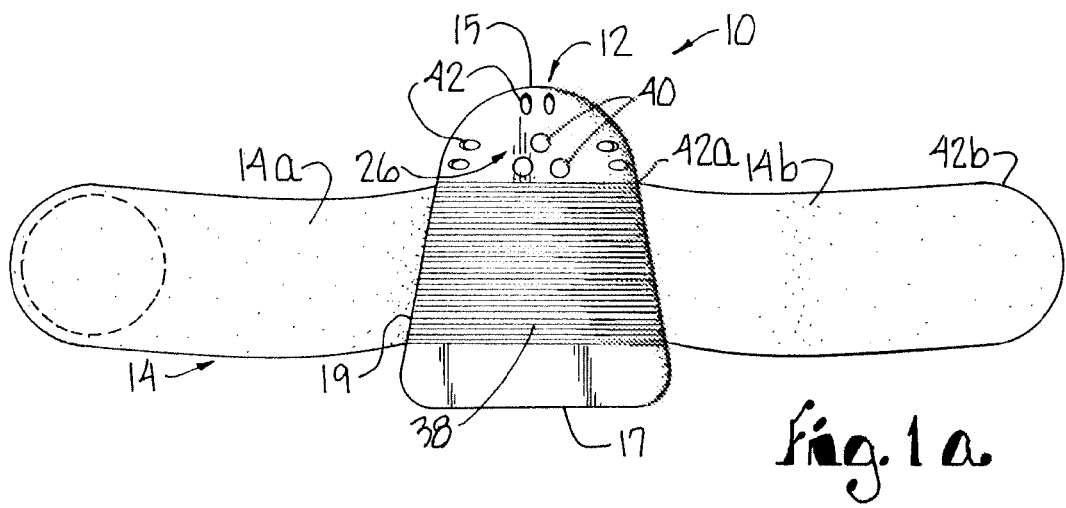
FIG. 1a is a plan view of the top of the site guard of the present invention, where the fabric connector is affixed to the lower edge and inner sidewall of the hollow member.

In general, the present invention relates to a site guard comprising a hollow member and a fabric connector having closure means to hold it in place over a site without applying adhesive to a patient's skin. The present invention may be embodied in many different forms. The discussion and drawings herein show a few specific embodiments with the understanding that the present disclosure is only an exemplification of the principles of the invention, and is not intended to limit the invention to the embodiments illustrated.

As used herein, "site" includes but is not limited to any wound, any opening, or any lesion in the skin, or more than one wound, opening or lesion, such as those made by needles and those made for peripheral or midline catheters, central venipuncture venous access catheters, tunneled catheters, nontunneled percutaneous central catheters; colostomy or ostomy bags, surgical drains; subcutaneous injections, pumps, subcutaneously implanted central venous access ports, implanted chest ports, implanted peripheral ports, subcutaneous implanted cardiac devices such as pacemakers and defibrillators; for AV fistulas, venous grafts or synthetic tubes used to create AV fistulas, or totally implanted dialysis access systems used in dialysis. "Site" includes accompanying equipment, for instance equipment present at an intravenous site: IV catheter, extension tubing, luer lock tubing, a loop of tubing, a catheter, locking mechanism (e.g. leur lock), extension tubing, transparent dressing, and tape, or wound, opening and lesion dressing materials such as gauze. Sites that may benefit from the present invention also include but are not limited by any cut or condition of the skin; and any cut or condition below the skin's surface that could benefit from surface protection, such as bone fractures, tissue swellings, burns, insect bites, excisions, sutures.

As used herein, hollow member 12 includes but is not limited to the portion of a site guard dimensioned so as to form a protective cover over a site, including a base with an edge to be positioned upon a patient's skin adjacent a site. Hollow members 12 may be made in a variety of shapes and sizes, such as elongate, circular, square, irregular or any other shaped bases and covers, and small sizes to fit neonates or small body parts. For sites that do not require an open-ended hollow member 12, for example sites without IV tubing, a fully closed hollow member 12 (FIGS. 7a, 7c) may be used to protect the site, as indicated by a health care provider.

As used herein, fabric connector 14 includes but is not limited to one or more pieces of any material, woven or non-woven, preferably breathable, including but not limited to a tubular material such as a mesh, stretch wrap, burn net, gauze, cotton cloths or blends, latex-free materials, soft cloth, Lycra, nylon, single or multiple phase polymeric materials such as Tyvek or polypropylene and polytetrahydrofluoroethylene (PTFE, made by Gortex®), tape wrap, a porous mesh, a stretchy fabric, a transparent material such as certain plastic or nylon or blends. Combinations of these materials are also contemplated, as is their treatment with porous polymers such as PTFE. For instance, the use of a porous fabric allows for better protection of patients' surface or subsurface injuries in humid environments, patients with a tendency to perspire, and patients who are active. A stretch wrap may also be useful for active patients, or those whose injuries are located in irregularly contoured areas. Additionally, the fabric connector 14 may include a material with sufficient stretch to allow the lifting of the hollow member so that the site may be inspected while the site guard is in use. A fabric connector 14 could be square, round, tubular, "X" shaped, or any other shape so long as it secures the hollow member to the patient.

One benefit of an "X" shaped fabric connector 14 is to avoid occluding one or more strategically placed ventilation holes. In use, a fabric connector 14 with excess material may be cut to size when a site guard is applied to a patient. Extended length fabric connectors 14 may be utilized for larger sized patients.

If the entire fabric connector 14 is opaque, a window 30 may be made to view a site through a transparent hollow member. Also, one or several openings 31 could be made in the fabric connector to accommodate other sites, or to accommodate body parts such as fingers, toes, wrists, ankles, elbows, eyes, ears or kneecaps, for example. A window 30, as well as an opening 31, may be square, round, "U" or "X" shaped, or any other useful or decorative shape. Models for right or left hands, for instance, may be made. By varying the size or shape of a site guard's hollow member 12 and size, shape, or material of its fabric connector 14, the site guard 10 may accommodate sites on any desired area of the body, such as infant scalps and extremities.

There are several embodiments of the fabric connector 14. Some fabric connectors 14 envelop one or more sites, the hollow member 12, and the surrounding area; while others comprise one or several straps including means for affixing 23 the hollow member 12 to the fabric connector 14 and means for closing 20 the fabric connector 14 so the entire site guard 10 is secured to a patient. The straps may be simple, such as the elongate fabric connector 14 pictured in FIGS. 1a and 6a, or more complicated such as being made in an "X" or "Y" shape (not shown). Affixing means 23 includes but is not limited to a way to fasten a fabric connector 14 such as a strap to the hollow member 12. Two or more straps together may secure the site guard 10 onto the patient. Other fabric connectors are permanently or removably affixed to the inner or outer dome, sidewalls, or lower edge of a hollow member. Affixing means 23 may include but is not limited to sewing, gluing, ultrasonic welding, chemical bonding, or using other means such as Velcro to affix the hollow member's 12 lower edge 16 onto a fabric connector 14, such as a cloth or plastic wrap-around dressing. In another embodiment, the hollow member 12 affixes to the fabric connector 14 by using gauze, flannel or other soft breathable cloth cut on a bias, doubled with a pocket the hollow member 12 can slide into.

Closure means 20 includes but is not limited to tape and other adhesives such as tape wrap, where fabric is against the skin and a peel-and-stick tape is on both ends, as well as non-adhesives such as hook-and-loop fasteners (Velcro®); Velcro ONE-STRAPs®; hook and eye fasteners, ties, pins, clips, hook and eye fasteners, ultrasonic welding or glue, and other suitable products. Closure means 20 are not limited to one shape or size; for instance, Velcro can take any form or shape; circle or square.

A fabric connector 10 may also incorporate or be coated with various agents. As used herein, an "agent" includes but is not limited to antimicrobial agents such as antifungal, antibacterial, or antiviral agents; aloe; vitamin E; lotions; burn salves such as Silvadine, or any other agent. Combinations of these agents may also be used. The amount of each agent used should be sufficient to have the desired effect without irritating the skin or have untoward side effects.

A preferred embodiment of the fabric connector 14 is two straps made of latex-free cloth that fit around an area and attach comfortably to a patient, without being tight or restrictive to medicine or blood flow. It has stretch and memory to retain its original shape, to provide a loose fit that stays in place. The straps attach to each other with some overlap, but do not wrap around the site in a circumferential manner. The ends of the straps are rounded, to avoid leaving unnecessary material for patients to pick at (such superfluous material is often called "dog-eared.") The preferred fabric connector 14 does not require any other fabric connector, such as an ace wrap or a cohesive type wrap that adheres to itself.

Site guards 10 may be stabilized and made more comfortable by cushioning the hollow member's base. Such cushioning may be achieved by affixing various materials to the base, such as cloth, gauze or Gortex-treated materials, or by flaring or otherwise altering the shape of the hollow member's base to make it more stable and comfortable against a patient's skin.

Other potential uses for this product include bracing or supporting bone fractures in areas where the use of casts is difficult or impossible, such as the face. The site guard 10 may be useful in outpatient or over-the-counter settings, for instance for a person with a bumped head to purchase to avoid irritating the bump while sleeping. Also, mammals and other animals may benefit from the present invention.

Figure 1B:
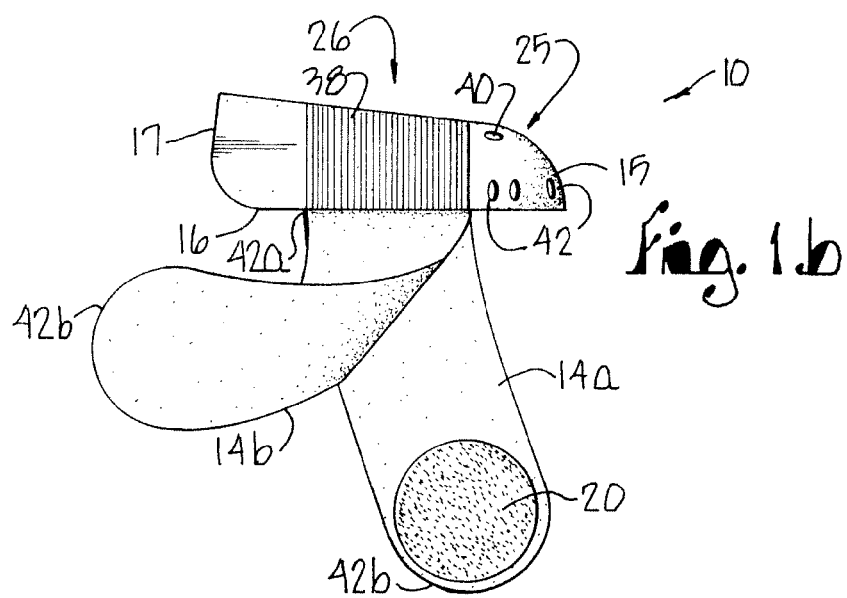
FIG. 1b is a perspective view of the site guard of the present invention.
Figure 1C:
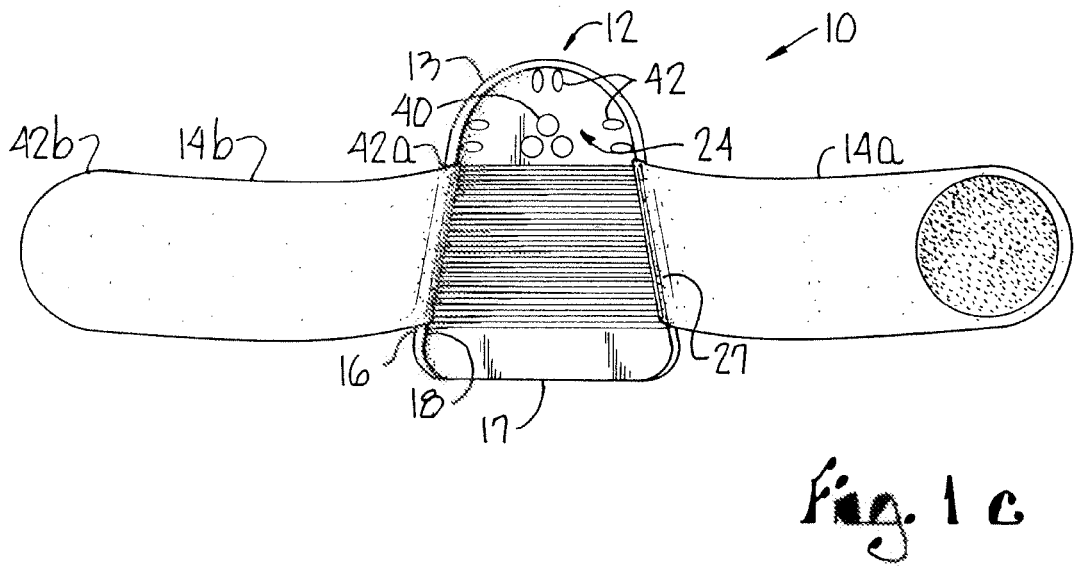
FIG. 1c is a plan view of the bottom of the site guard of the present invention.
Figure 1D:
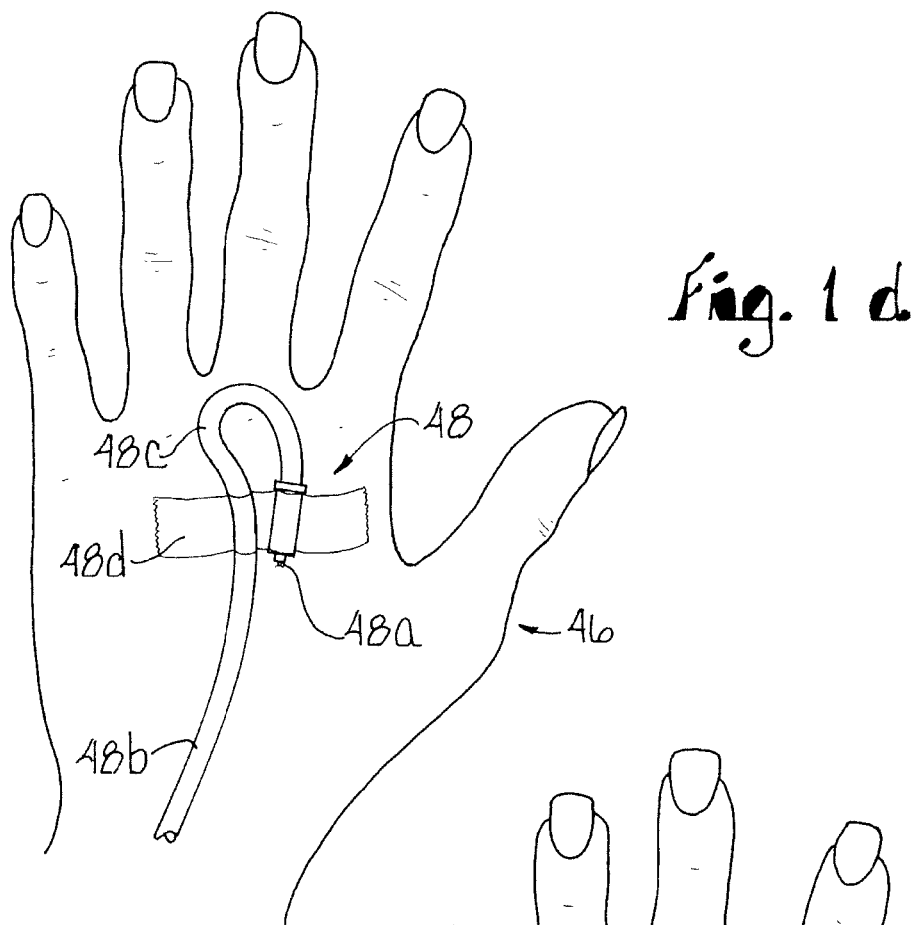
FIG. 1d is a plan view of a hand with a site.
Figure 1E:
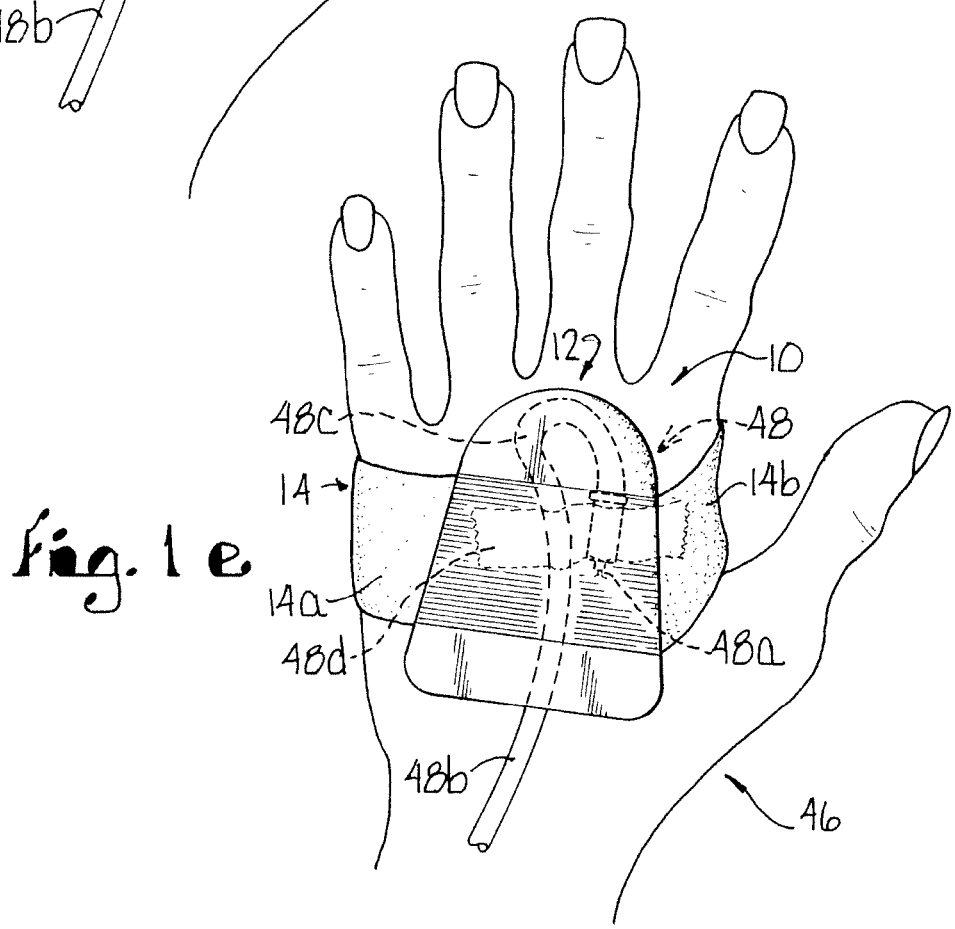
FIG. 1e is a plan view of a hand with a site covered by a site guard.

The accompanying drawings illustrate several embodiments of a site guard indicated by reference numeral 10. As illustrated in FIG. 1a-c, the site guard 10 is comprised of a hollow member 12 and a fabric connector 14. FIG. 1a-c illustrate a hollow member 12 that is structurally simple and functionally elegant. It comprises a fabric connector 14 and a hollow member 12 having a U-shaped base 13 with a generally planar lower edge 16. The U-shaped base 13 is joined to sidewalls 18, 19 curved upwardly and inwardly to form a cover 25 with a open end 15 and an closed end 17. The U-shaped base 13 has a width sufficient to straddle a site 48, for instance a site including a needle or catheter 48a (as shown in FIGS. 1d-1e), inserted into a vein of a patient where the site 48 also includes a loop of tubing 48c, transparent dressing, and tape 48d. The U-shaped base has a length sufficient to cover the site 48 and a height sufficient to provide a space between the inside of the inner dome 24 of the hollow member 12 and the site 48. Another useful embodiment and method for using the site guard 10 includes positioning the hollow member 12 on a patient, where the hollow member 12 has an elongate open end 15 and the U-shaped base 13 is elongated or split into two legs that may lay flush against the patient's skin (not shown).

Hollow members 12 may be of any size so as to accommodate different sizes of sites 48. For instance, a small site guard 10 has a width of up to about 1.5 inches, a length of up to about 1.5 inches, and a height of up to about 0.5 inch. A large site guard 10 has a width of up to about 2.5 inches, a length of up to about 2.8 inches, and a height of up to about 0.8 inches. Other hollow member 12 dimensions may be useful to protect other sites 48, especially those sites 48 with equipment such as IV equipment 48a-48d, extension sets, Statlocks or Veniguards. Smaller hollow members 12 may be used to accommodate neonates or small animals, and larger hollow members 12 used to accommodate adults or large animals. Both sizes may be used on patients of any age or animals of any size. The hollow member 12 size is determined by the area of the site it encompasses, but is not intended to encompass an entire body or limb. Its dimensions are limited by the size and shape of the base, which contacts patients' skin, and the height of the dome, which protects without becoming unwieldy.

Once the hollow member's dimensions are set, for example to the size of the small or large site guards described above, in use it will stabilize and standardize the size of the loop of tubing 48c used in sites such as IV sites. Stabilizing the loop of tubing 48c decreases IV therapy problems caused by loops that are too wide or too long. The loop must fit under the hollow member 12 of such sites 48; while varying sizes of tubing 48b and loops 48c may be used, they cannot exceed the dimensions set by the hollow member 12.

Use of the present invention will increase dwell time in patients by decreasing the mechanical manipulation of, for instance, a catheter 48a at a site 48 or loop of tubing 48c.

Anecdotal evidence showed catheters 48a protected by site guards lasted four to five days in pediatric (less than 18 year old) patients. Accordingly, the site guard 10 can increase dwell time in patients.

The hollow member 12 is formed of a plastic material stiff enough to cushion a site 48 from a blow, and flexible enough such that the open end 15 can be spread when finger pressure is applied to the cover. To facilitate spreading of the open end 15 to conform the hollow member 12 to the site 48 and to avoid gouging the patient's skin, it is preferred that the open end 15 be outwardly flared and that the sidewalls 18, 19 be curved at the open end 15 of the hollow member 12 as it joins the U-shaped base 13.

One suitable material for making the hollow member 12 which satisfies the above-mentioned specifications is medical grade low density polyethylene from which a 0.030 inch thick hollow member 12 is manufactured by injection molding and thermoforming. Other materials and processes, including but not limited to vacuum molding and thermoforming, may be selected to make a rigid or soft or transparent site guard 10. For instance, if a site did not require a flexible hollow member 12, the hollow member 12 could be thermoformed of a polypropylene material to increase its transparency.

For the purpose of visualizing a site 48 through the hollow member 12 it is preferred that the material comprising the hollow member be transparent or semi-transparent. Transparency is important since the site guard 10 not only acts as an enclosure but also allows visual inspection of the site 48, of the condition of the skin surface immediately around the site, and, if present, of needle or catheter 48a and surrounding areas. The fabric connector 14 may complement this transparency by being transparent itself.

In every embodiment of the present invention, the site guard 10 may include one or more windows 30 in the fabric connector 14 for viewing the site 48 or to avoid harming sites 48 that would otherwise be covered by the fabric connector 14; one or more openings 31 to accommodate digits or other body parts otherwise covered by the fabric connector 14, or as otherwise desired; one or more channels 36 or 38 (for example, as shown in FIGS. 3a, 4a, 5a, 5c), in the hollow member 12 to help retain the fabric connector as placed with the hollow member 12; ventilation holes 40 in the hollow member 12 to keep the site aerated and otherwise control the environment inside the hollow member 12; antimicrobial or agents; and a cushion 27, 28 on the lower edge 16 of the hollow member 12, in addition to any other accessories indicated or their equivalents. Also, the outer portion 42b of single 14a or opposing straps 14a, 14b, or other portions of a fabric connector 14 may be bifurcated or otherwise splayed; long or short; rounded, flared, tapered, or otherwise shaped. Splayed fabric connectors 14 may be particularly useful for accommodating fingers or other body structures in fastening the site guard 10 to a patient. Site guards 10 may also sport different colors or designs, for example for decorative or classification purposes.

As shown in FIGS. 1a-1c, the hollow member 12 may provide the site with ventilation. Ventilation is desirable for reasons including but not limited to facilitating an exchange of air to prevent the formation of moisture vapor. Hollow members 12 may be made with one or more ventilation holes 40, preferably in its top and/or sidewalls and preferably its closed end 17. However, a ventilation hole 40 may be placed anywhere on the hollow member 12, and the hollow member 12 may be altered (for instance, by texturing and depressing a means for retaining the fabric connector 14) to enhance ventilation. A ventilation hole 40 may be made in a variety of shapes and sizes, including but not limited to circular, oblong, oblate, elongate, rectangular, square, triangular, or grid-like (for instance, like a screen); as well as being made with a third dimensional variation such as rectangular strips turned inward. Also, a ventilation hole 40 may be covered with a porous material (not shown), such as a plastic grid, nylon mesh, and the like, to provide further protection of the site 48 from invasive particulate or other matter. Alternatively, the site guard 10 may be completely without a ventilation hole 40.

A preferred embodiment of the site guard 10 is a fully ventilated device where the hollow member's 12 lower edge 16 may be affixed to a fabric connector 14 with an affixing means 23. In one embodiment, the site guard 10 may include ultrasonically welding a fabric connector 14 to a hollow member 12, where the hollow member's 12 lower edge 16 has a flat flange shape. Another embodiment may entail affixing a polyethylene hollow member 12 to a polypropylene fabric connector 14 with a cyanoacrylate system.

As shown in FIGS. 1a-1c, a site guard 10 may be provisioned with a retainer 36 to retain a fabric connector 14 to help secure the site guard 10 to a patient. For example, the retainer 36 may be located in the cover 25 between the open end 15 and closed end 17 of the hollow member 12 and may be a channel formed in the hollow member 12. The channel may be smooth or grooved or otherwise textured or shaped to help secure a fabric connector 14 in place. As defined herein, a retainer 36 for the fabric connector 14 includes but is not limited to a structure equivalent to a channel, such as guiding hooks or half or whole "belt" loops, or could include one or more smaller deeper channels within a larger channel for retaining fabric connectors 14 of varying widths (not shown).

As seen in FIG. 1c, the fabric connector 14 comprises two opposing straps 14a, 14b, each strap having an inner portion 42a affixed to the lower edge 16 and inner sidewall 18 of the hollow member 12. An outer portion 42b includes closure means 20 in the form of a Velcro strip. The dimensions of the opposing straps 14a, 14b of this fabric connector 14 are at least about three inches long, and at least about one inch wide. Circular and oval top and side ventilation holes 40 help aerate the site 48. The site guard 10 fabric connector 14 in these illustrations is made of stretch wrap that fastens to the closure means 20, so the relative tightness of the fabric connector 14 may be easily adjusted. In this and several other embodiments of the invention, the site guard 10 may be easily disengaged from the patient by removing part or all of the fabric connector 14 from the hollow member 12, or by disengaging the site guard 10 from the patient. The integrity of a site 48, and if present a site's 48 needle or catheter 48a, loop of tubing 48c or other accompanying equipment, as well as the patient's skin, may be inspected, treated or adjusted, and the site guard 10 easily remounted. By protecting the site 48, while leaving it readily available for inspection either through the cover 25 or with the cover removed, the number of IV restarts is reduced. The reduction in IV starts reduces patient discomfort and lowers medical costs.

The illustration in FIG. 1c shows that the hollow member's 12 lower edge 16 may have a means for spreading the weight of the hollow member 12 across a patient's skin once approximately placed over a site. Flaring (FIGS. 18a and 18b) or any other modification of any part of the hollow member 12 that directly contacts the skin may act as a "cushion" to further protect the patient's skin or body. The lower edge 16 may be partially cushioned 27 or entirely cushioned 28. For instance, as shown in FIG. 1c, the inner portions 42a of the fabric connector 14 form a partial cushion 27 of the lower edge 16 of the hollow member 12. Covering the lower edge 16 in this way comfortably cushions the patient's skin from direct contact with the lower edge 16. Material to cushion the lower edge 16 of a hollow member 12 may be made of, but is not limited to, soft porous cloth, gauze, stretch wrap, foam tape, or other suitable substance. Such material is affixed to the hollow member through removable or permanent affixing means 23 like Velcro, sewing, gluing, ultrasonic welding, and any other means for attaching the fabric connector 14 to the hollow member 12. Alternatively, a separate cushion 27, 28 may be added to increase patient comfort. The cushion 27, 28 may completely surround the base 13 or flange 230 of the hollow member 12, may be U-shaped, may line only the lower edge 16, or be placed in any other position that would increase the comfort of the site guard 10 or assist in cushioning blows to the site guard 10 on a patient. Further, several layers of cushion 27, 28 may be used with each other.

FIG. 1*d* shows a hand with an IV site 48, and FIG. 1*e* shows the site guard 10 assembled over the site 48. In FIG. 1*d*, the loop 48*c* extends up among the fingers of an IV patient's hand, then hangs off of the side of the hand. In FIG. 1*e*, the hollow member 12 controls the size of the loop of tubing 48*c*, and prevents unnecessary pulling or other movement of the tubing 48*b* near the puncture area 48. Currently, nurses are instructed to loop 48*c* the tubing 48*b* back and secure the tubing with tape 48*d*. A loop of tubing 48*c* that is too wide or long creates problems in IV therapy. The hollow member's size and shape stabilize and standardize the size of the loop 48*c* and tubing 48*b* used, and thus decrease some IV therapy problems. Adherence to directions facilitates training nurses in the use of this invention without criticizing current practices.

In use, as shown in FIG. 1*e*, a site guard's 10 hollow member 12 may conform to one or more sites 48 on a hand 46. The hollow member 12 may also conform to venipuncture sites 48 on adults and, on a smaller scale, on infants. The flexibility of the plastic cushions blows on the hollow member 12 with a gradual resistance such that the site 48 is protected, the friction joint between hub and tapered part of hub is not broken, and if present the needle or catheter 48*a* is protected from displacement. There is a decreased chance of snagging the needle or catheter 48*a*, which gives the patient a sense of security. Under the protection of the hollow member 12, tubing 48*b* and other site apparatus, or an extension set that allows infusing through the hub about six inches away from the catheter hub (not shown) rather than directly into the hub on the patient's skin, is separably connected to the hub of a needle or catheter 48*a*. A setup for a particular patient may or may not employ an extension set. For intermittent use, the hub can be capped with a locking plug (not shown) and the supply line disconnected.

Figure 2A:
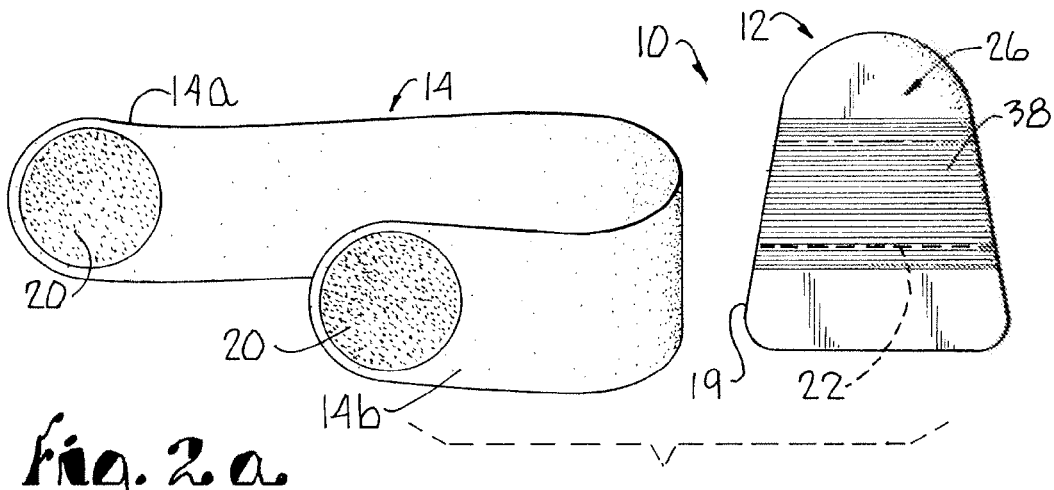
FIG. 2a is a plan view of the top of the site guard of the present invention, where the fabric connector is completely separate from the hollow member.
Figure 2B:
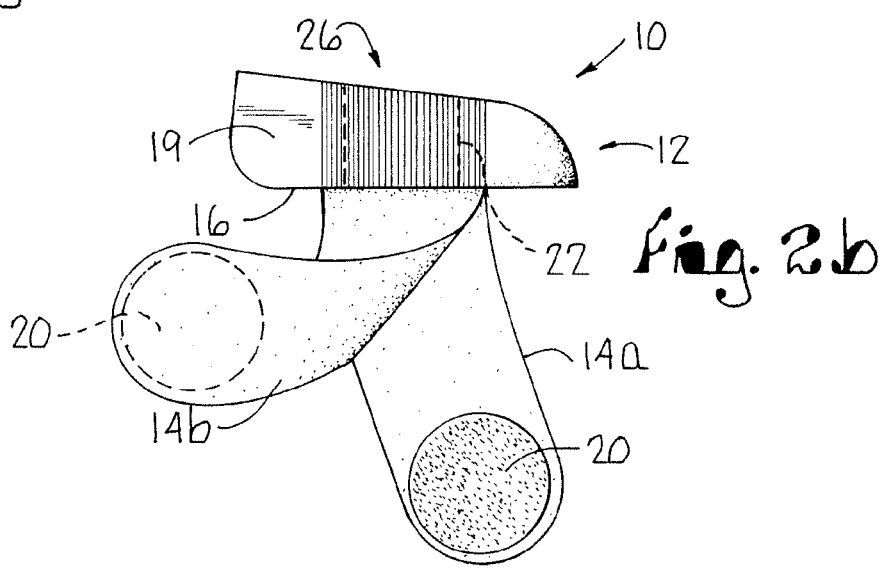
FIG. 2b is a perspective view of the site guard of the present invention, where the fabric connector is removably affixed to the inner dome of the hollow member.
Figure 2C:
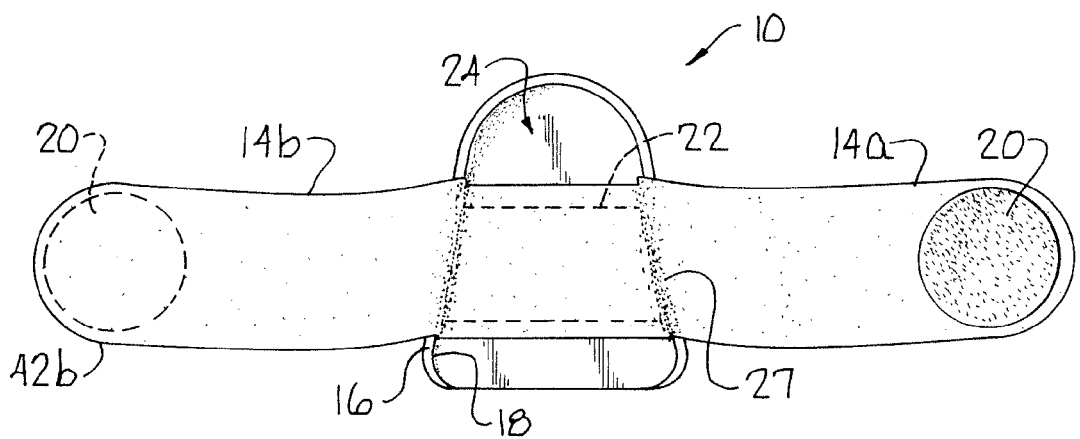
FIG. 2c is a plan view of the bottom of the site guard of the present invention, where the fabric connector is removably affixed to the inner dome of the hollow member.

The fabric connector 14 in FIG. 2*a* is completely separate from the hollow member 12; in FIGS. 2*b* and 2*c*, the fabric connector 14 is affixed to the interior of the hollow member 12. FIG. 2*c* shows that the hollow member 12 has affixing means 23 attached to its inner dome surface 22. In this embodiment, the affixing means is a hook and loop fastener like Velcro. The fabric connector 14 is pressed against the closure means 20 located on the inner dome surface 22 in the hollow member 10 to form a site guard 10 that can be placed over a site 48. The fabric connector's opposing straps 14*a*, 14*b* may be stretched to comfortably secure the hollow member 12 to a site 48, using closure means 20 such as Velcro strips on the outer portions 42*b* of the fabric connector 14. A fabric connector 14 affixed in this way to the hollow member 12 automatically creates a partial cushion 27 on the lower edge 16.

The site guard 10 embodiment illustrated in FIGS. 3*a-c* is similar to that of FIG. 1*a-c*. For instance, it may include ventilation holes 40 in the hollow member 12 as described for the embodiment shown in FIGS. 1*a*-1*c*. However, in FIGS. 3*a-c* the fabric connector 14 is large enough to cover the entire length and width of the hollow member 12, and is affixed to the lower edge 16 of the hollow member 12. The dimensions of the opposing straps 14*a*, 14*b* of this fabric connector 14 are of a length and width sufficient to accommodate any. To accommodate the site 48, a window 30 is cut out of the fabric connector 14, as seen in FIG. 3*c*. The window 30 also preserves the transparency of the hollow member 12, so the site 48 may be fully viewed through the hollow member 12 at all times. The window 30 also creates a complete cushion 28 around the entire lower edge 16 of the hollow member 12 by using the fabric connector 14 as a cushion. Such a cushion may improve the stability of a site guard 10 and create a more comfortable fit on the patient's skin. As in the other examples, the opposing straps of the fabric connector 14*a*, 14*b* may be stretched to secure the site guard 10 over the site 48 and closed with closure means 20.

Figure 4A:
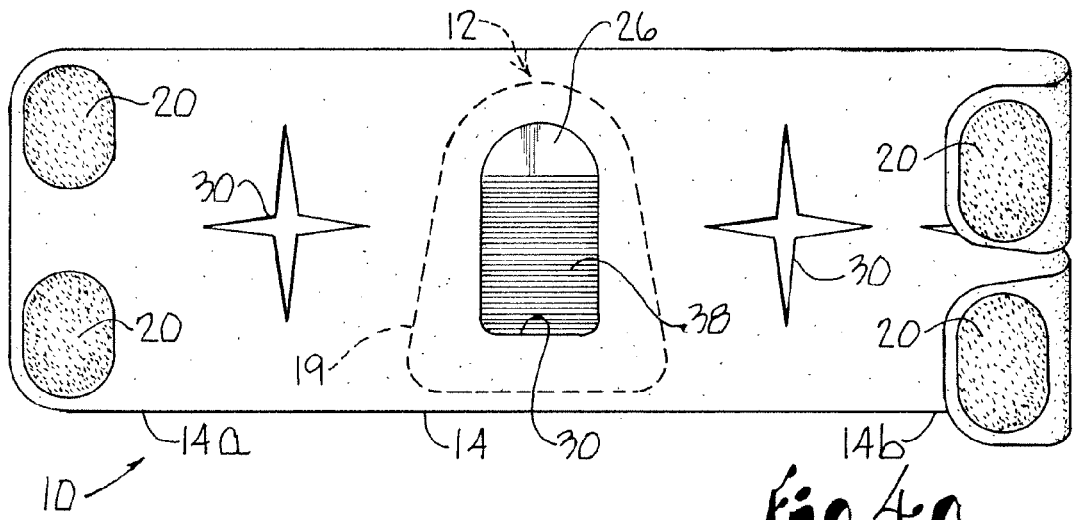
FIG. 4a is a plan view of the top of the site guard, with the fabric connector affixed to the outer sidewall of the hollow member.
Figure 4B:
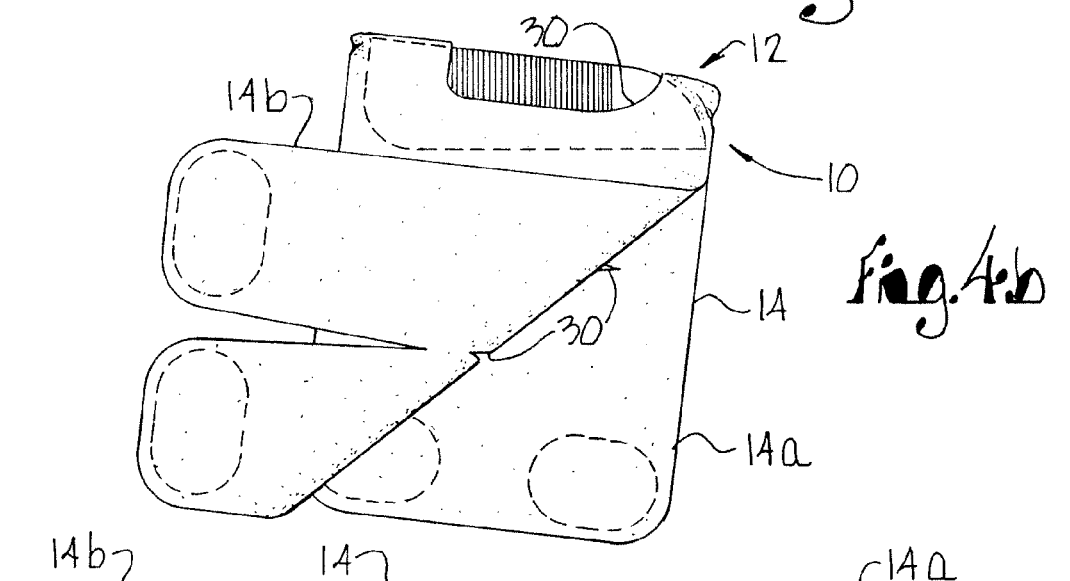
FIG. 4b is a perspective view of the site guard of the present invention.
Figure 4C:
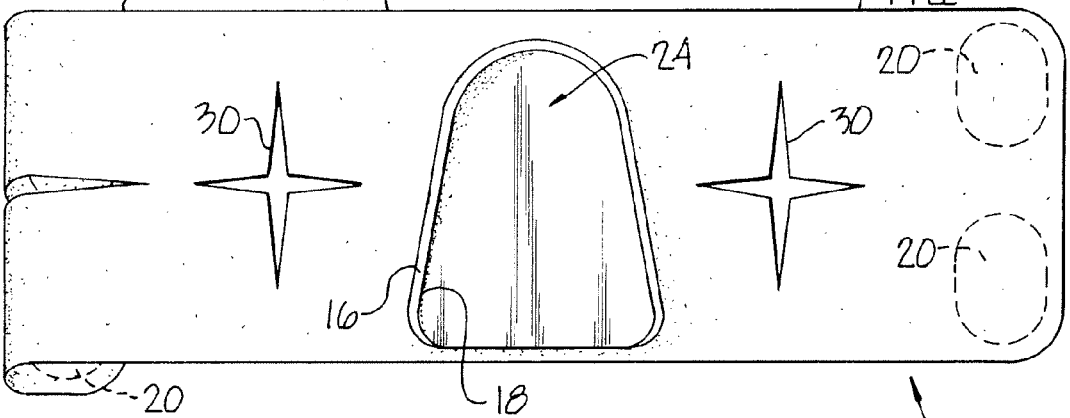
FIG. 4c is a plan view of the bottom of the site guard of the present invention.

FIGS. 4*a-c* shows another embodiment of the invention, where the fabric connector 14 is affixed to the outer side walls 19 of the hollow member 12 and may cover the hollow member 12 only a little or not at all. A window 30 allows for viewing of a site 48. The openings 31 in the opposing straps 14*a*, 14*b* of the fabric connectors may accommodate other sites or body parts, and closure means 20 close the straps to secure the site guard 10 over a desired site 48. Additionally, the fabric connector 14 may be transparent. One strap 14*b* is bifurcated to allow for greater flexibility in adjusting the fabric connector 14.

Figure 5A:
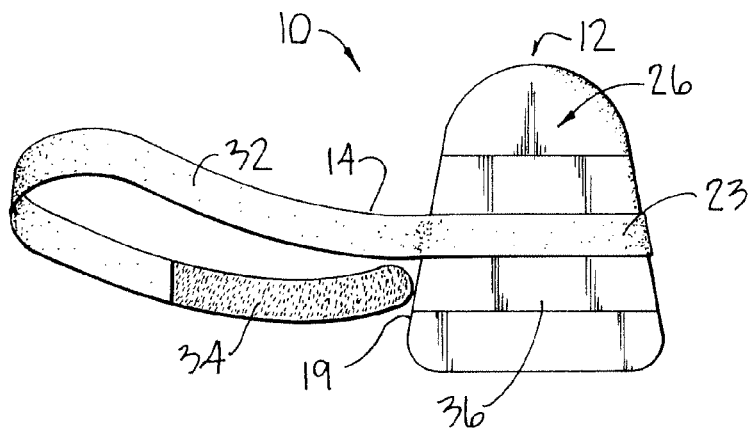
FIG. 5a is a plan view of the top of the site guard of the present invention, where the fabric connector may be removably affixed to the outer dome and outer sidewall surfaces of the hollow member.
Figure 5B:
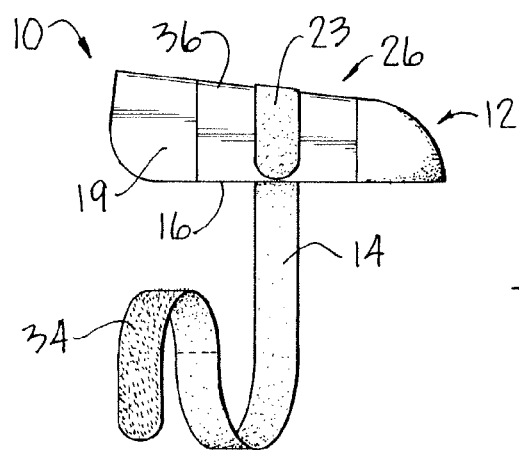
FIG. 5b is a perspective view of the site guard of the present invention.
Figure 5C:
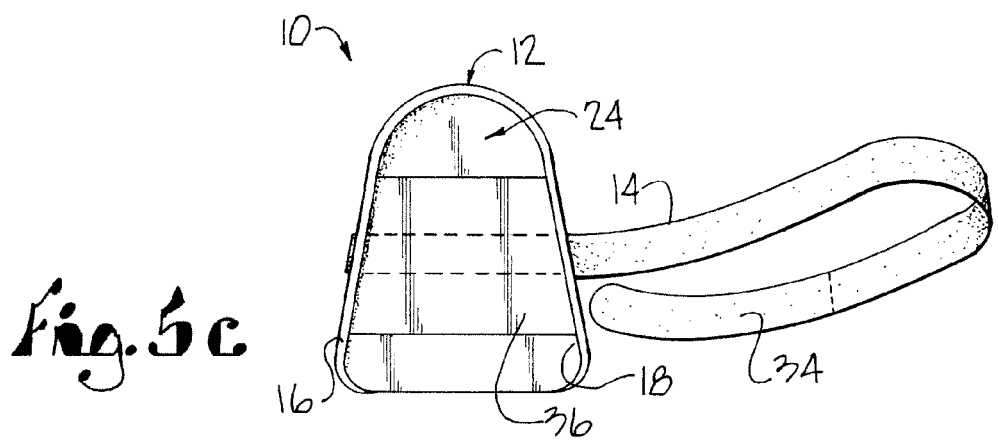
FIG. 5c is a plan view of the bottom side of the site guard of the present invention.

FIG. 5*a* illustrates a plan view of the top side of the site guard of the present invention, where the fabric connector 14 may be removably affixed to the outer dome 26 and outer sidewall 19 surfaces of the hollow member 12. The applicants demonstrate the use of a Velcro ONE-WRAP strap as the fabric connector 14, where Velcro is affixed to the outer dome 26 surface and sidewalls 19 of the hollow member 12. The remainder of the strap is a fabric with a smooth surface 32 and a textured surface 34 that fastens to the Velcro strip, as shown in use in FIG. 5*d*. The hollow member 12 may thus be secured over a site 48 simply by fastening the textured surface 34 to the Velcro strip. In use, as shown in FIG. 5*d*, a site guard's 10 hollow member 12 may conform to one or more sites 48 on a hand 46 or to venipuncture sites 48 on adults and, on a smaller scale, on infants.

Figures 5D, 6A:
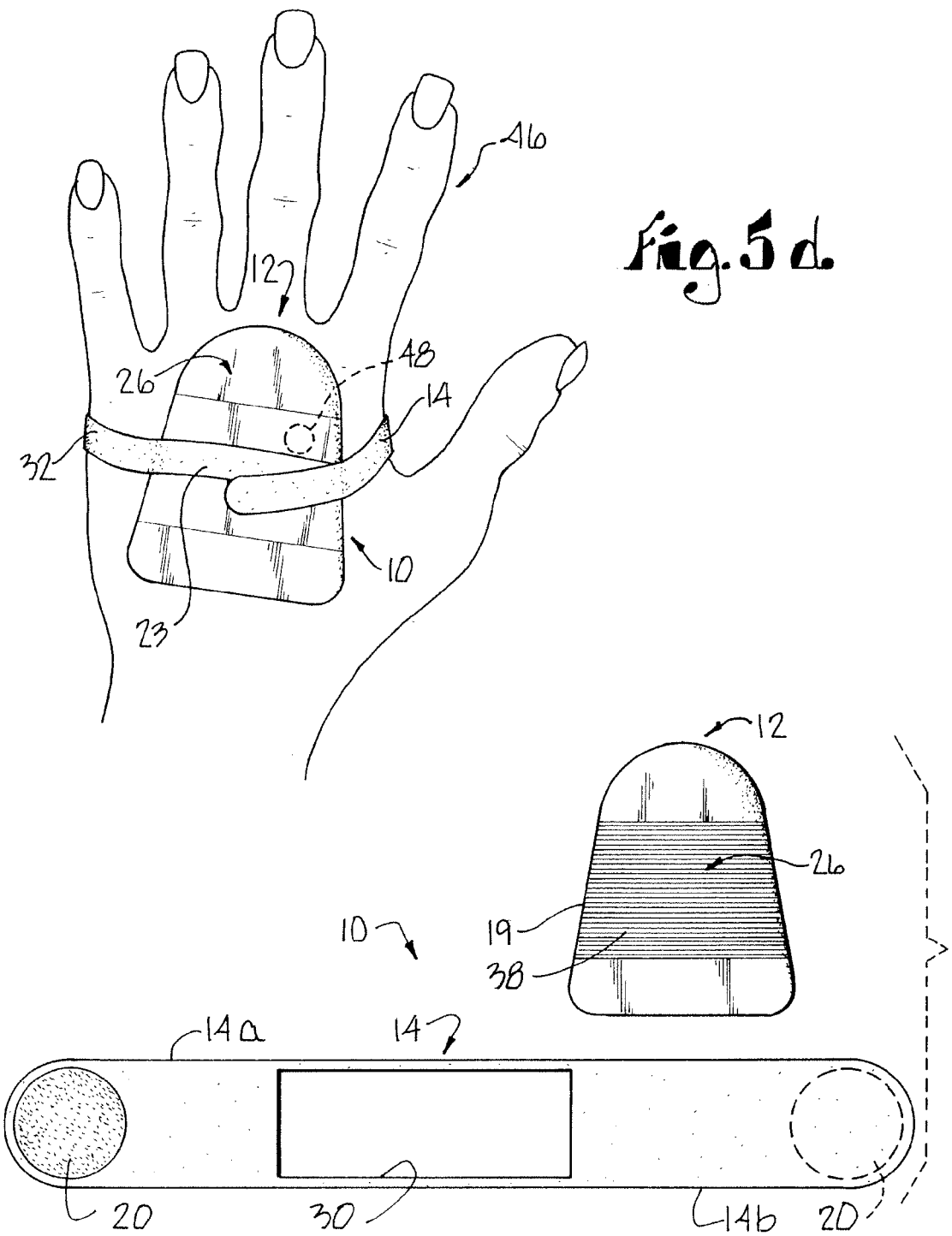
FIG. 5d is a plan view of the site guard covering a site on a hand.
FIG. 6a is a plan view of the top of the site guard of the present invention, where the fabric connector is completely separate from the hollow member.

FIG. 6*a* illustrates an embodiment of the invention where the fabric connector 14 is not permanently affixed to the hollow member 12. FIG. 6*b* shows the assembly of the site guard 10 over a site 48 on a patient's hand 46. First, a hollow member 12, with or without a cushioned base 27, 28, is placed over a site 48 such that the site and its accompanying tubing 48*b* and other items fit under the hollow member 12. Then a fabric connector 14 with opposing straps 14*a*, 14*b* is placed over the hollow member 12 and secured to the hand with closure means 20 on the outer portions 42*b*. A channel 38 in the hollow member 12 guides the fabric connector 14 to keep it from becoming displaced. A window 30 in the fabric connector 14 positions over the transparent hollow member 12 so the site 48 can be easily viewed. An additional Velcro strip may be placed directly on the outer surface of the hollow member 12 may be used to more fully secure the fabric connector 14 to the hollow member 12.

Figure 7B:
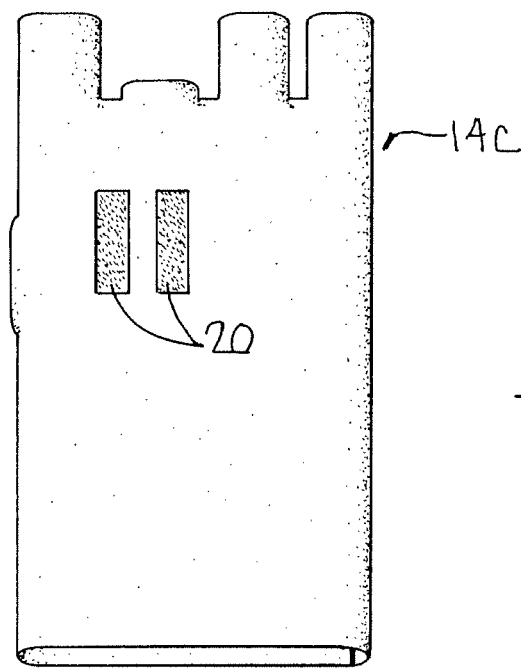
FIG. 7b is a perspective view of a tubular fabric connector, turned inside-out to expose Velcro strips inside the fabric connector.
Figure 7C:
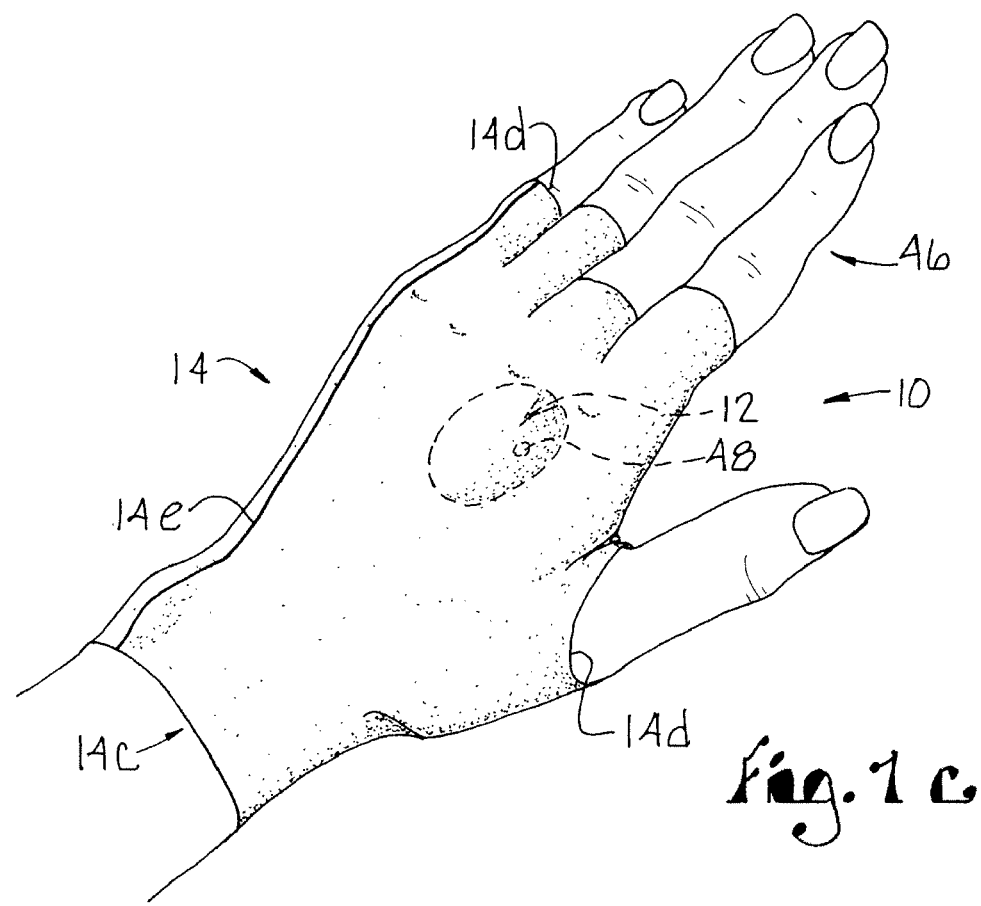
FIG. 7c is a perspective view of the site guard of the present invention, completely assembled, with the fabric connector affixed to the hollow member.

FIGS. 7*a-c* illustrate another embodiment of the present invention. FIG. 7*a* shows a completely closed hollow member 12 with a round base and lower edge 16, and a separate fabric connector 14 made of a delicate white tubular mesh 14*c*. The hollow member 12 may include ventilation holes 40 as described for the embodiment shown in FIGS. 1a-1c. The fabric connector 14c could be made of any tubular material capable of enveloping a patient's entire hand 46, or any other body part as needed. If a site 48 does not include IV tubing 48b or other apparatus that requires an open end to the hollow member 12, the hollow member 12 may still have one or more open ends, or be fully closed as shown here. The lightweight mesh 14c must be tight enough to secure the guard but not so tight as to cause patient discomfort. As seen in FIG. 7b, where the tubular mesh 14c is turned inside-out, the tubular mesh 14c has affixing means 23 that will match up with affixing means 23 on the outer portion of the hollow member 12 (FIG. 7a), to affix the fabric connector as seen in FIG. 7c. In use, as shown in FIG. 7c, a site guard's 10 hollow member 12 may conform to one or more sites 48 on a hand 46 or to venipuncture sites 48 on adults and, on a smaller scale, on infants.

FIG. 7c shows the fully assembled site guard 10, where the fabric connector 14c completely envelops the hollow member 12 and surrounding area of the patient's hand and wrist. Other means for affixing 23 the fabric connector 14c to the hollow member 12 may also be used. Varying grades of mesh may be used, with the size of the mesh and weight of the material varying with the degree of support needed and the sensitivity of the patient's skin. A window 30 could be made in the fabric connector 14 if the mesh was too dense to allow for viewing of the site. This embodiment provides an exceptionally useful means for securing a hollow member 12 to burn patients, since it is very lightweight, easily removed by cutting, and less dense than fabric connectors 14 comprised of straps. This embodiment of the site guard 10 slides easily under covers, loose clothing, and various wraps, where it can be worn (for instance by IV patients between treatments) without detection and with discretion to protect the patient's right to privacy regarding treatment and illness. The preferred embodiment of this type of site guard 10 is a fabric connector 14 of tubular mesh 14c and of the size to cover a patient's hand and portions of the patient's fingers and wrist. The tubular mesh 14c may have different diameters openings 31 to comfortably fit varying sizes of wrists and fingers. The mesh covering the fingers may be cut to various lengths; in the picture, the mesh covering the thumb and middle finger is shorter than the mesh covering the remaining fingers. Fabric connectors 14 may be made to be aesthetically pleasing. In FIG. 7c, a colored stripe 14e runs along the tubular mesh 14c from the wrist to the fingers.

Other embodiments of this particular version could include having a ½ length tubule of burn netting permanently or removably attached to the lower edge 16 of the hollow member 12. The fabric connector 14 could be made of stretch wrap or of some more rigid cloth, such as the type that could be comfortably opened, closed and adjusted with criss-cross ties like corset strings. Also, a fabric connector 14 could be opened and attached to the base 16 or sidewalls 18, 19 of the hollow member 12, creating an embodiment similar to FIGS. 1a, 3a and 4a, but where the straps are continuous (not shown).

The embodiment shown in FIG. 7c may also include a partial or total cushion (not shown). In this embodiment, uses for a partial 27 or total cushion 28, other than those previously discussed, include monitoring and helping control the moisture inside the hollow member 12. Although this function is useful in any of the embodiments, it is especially useful for an embodiment including a completely closed hollow member 12 or a hollow member 12 fully enveloped by a fabric connector as is shown in FIG. 7c. Site guard cushions 27, 28 may be removably or permanently affixed to the hollow member 12, depending on the type of material the cushion is made from, whether it is part of the fabric connector 14, and the perceived needs of the applicants.

The site guard can also be affixed to an arm board of various lengths using the connectors presented herein. Such arm boards are frequently used in pediatric patients and may run from the hand to the wrist or from the hand to the elbow.

Figure 8:
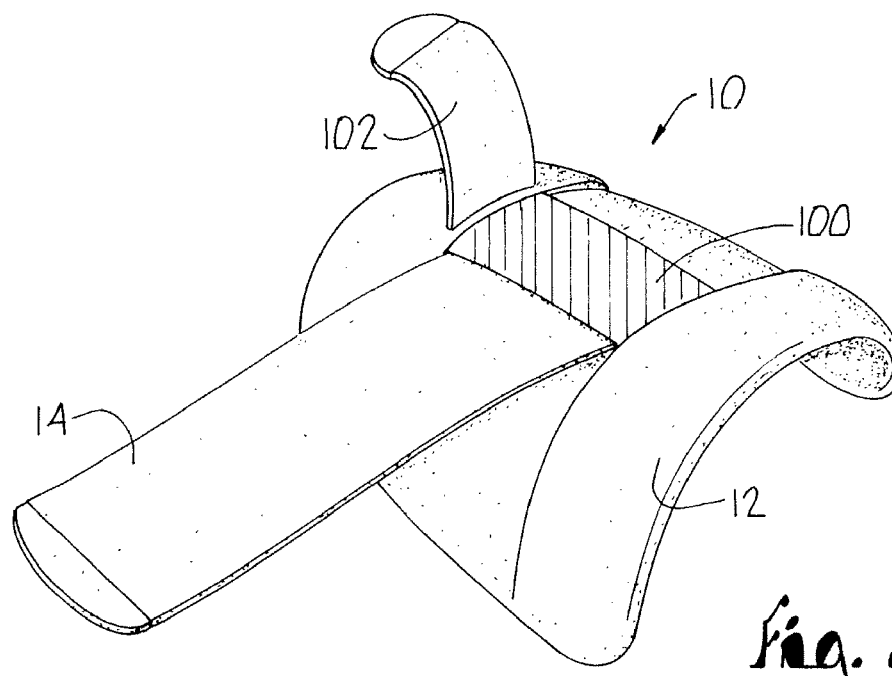
FIG. 8 is a perspective view of an embodiment of the site guard.

In another embodiment (FIG. 8), the fabric connector 14 comprises a single strap made from stretch fabric or other stretchable material. The fabric connector 14 is attached to the top of the hollow member 12. The fabric connector 14 wraps around the desired body part and attaches to an adhesive 100 or Velcro located on the top of the hollow member 12. The tension created by the fabric connector 14 helps to hold the site guard 10 in place. Prior to and when not in use, the adhesive 100 is covered by a strip 102 that can be removed without destroying the adhesive properties of the adhesive. Alternatively, the fabric connector 14 may comprise a bifurcated or double strip that is attached to either the inner 18 or outer 19 sidewall.

In other embodiments (FIGS. 9-13), the fabric connector 14 comprises a single strap with a plurality of holes 110. In use, one of these holes 110 mates with a tab 115 located somewhere on the site guard 10. These embodiments enable the site guard 10 to be used on body parts or patients of various sizes by mating the appropriate hole 110 with the tab 115. Furthermore, the fabric connector 14 can be made of a stretchable material to ensure an even better fit and alignment of the site guard 10.

Figure 9:
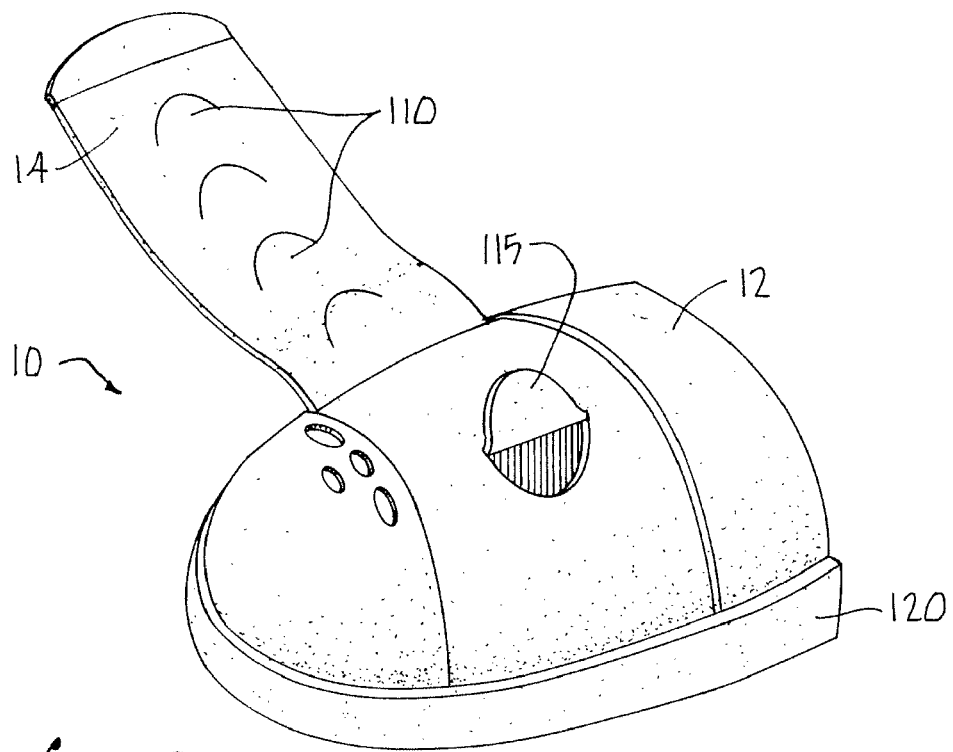
FIG. 9 is a perspective view of an embodiment of the site guard.
Figure 10:
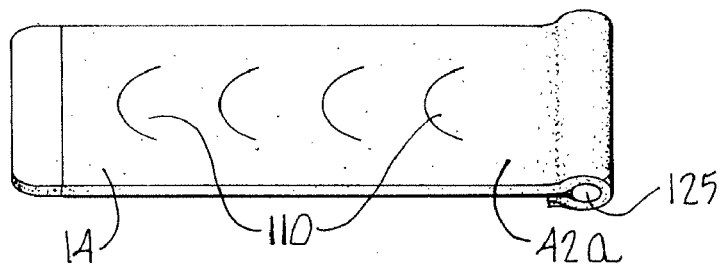
FIG. 10a is a perspective view of an embodiment of the fabric connector.
FIG. 10b is a perspective view of an embodiment of the site guard.
FIG. 10c is a back plan view of an embodiment of the site guard.
Figure 10:
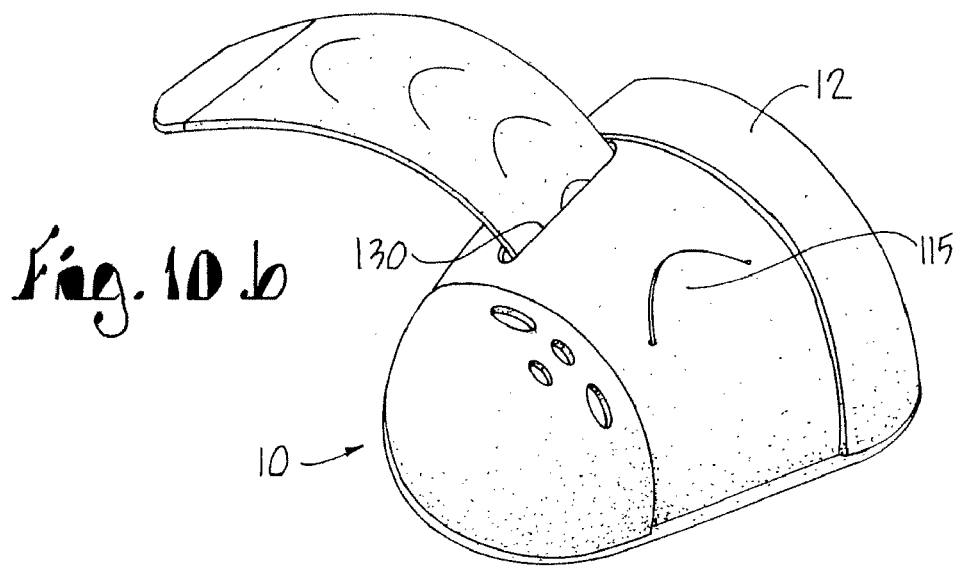
Figure 10:
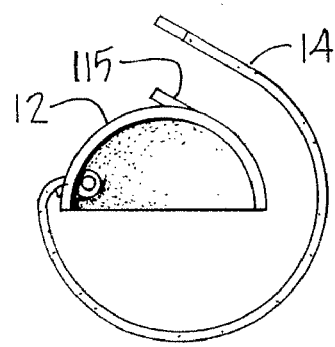

In FIG. 9, the fabric connector 14 includes a plurality of holes 110. The lower portion of hollow member 12 includes a strip of fabric 120 to which the fabric connector 14 is stitched or otherwise attached. In use the fabric connector 14 wraps around the desired body part and one of the holes 110 mates with the tab 115 to securely, but not too tightly, secure the site guard 10 to the patient.

FIGS. 10a-c, show an embodiment similar to the one shown in FIG. 9. In use, the fabric connector 14 includes a plurality of holes 110 that mate with a tab 115 on the hollow member 12. Additionally, the fabric connector 14 includes a doubled-over portion 125 on its inner portion 42a. The inner portion 42a is attached to the hollow member 12 by inserting the fabric connector 14 into a slot 130 in the hollow member 12 (FIG. 10b). The doubled-over portion 125 prevents the fabric connector 14 from being pulled completely through the slot 130, as shown in FIG. 10c. Alternatively, the doubled-over portion can be formed after the fabric connector 14 has been inserted into slot 130 and formed so that it wraps around the lower portion of the hollow connector 12, thereby forming a loop around the lower portion.

Figure 11:
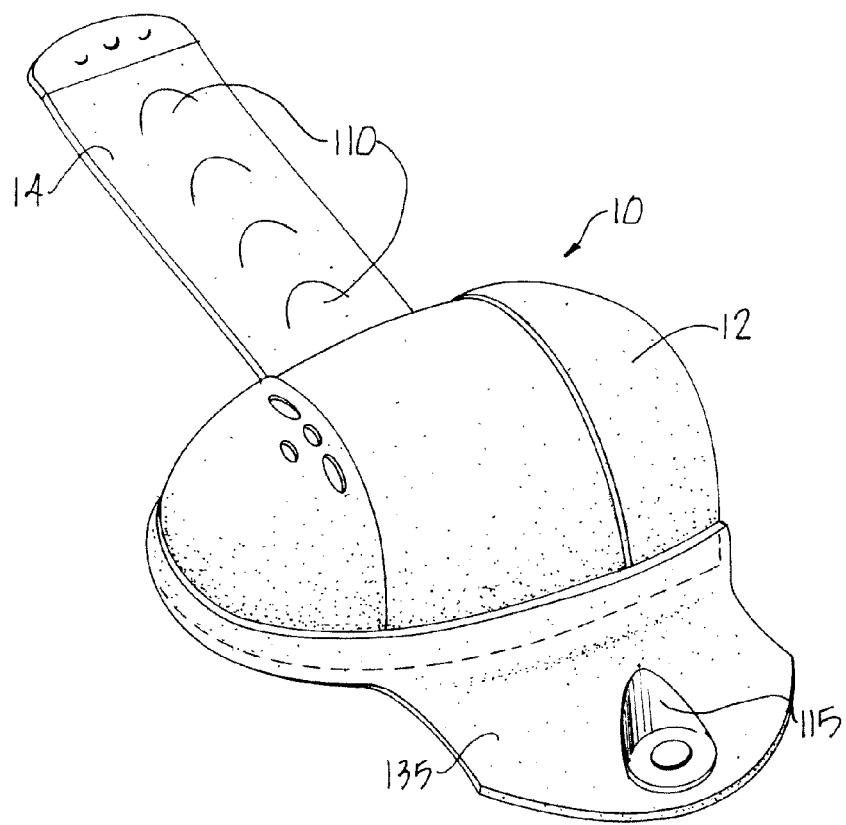
FIG. 11 is a perspective view of an embodiment of the site guard.

FIG. 11 also shows an embodiment similar to the one shown in FIG. 9. In use, the fabric connector 14 includes a plurality of holes 110 that mate with a tab 115. The hollow member 12 includes a side extension 135 attached to the side of the hollow member 12 opposite the side to which the fabric connector 14 is attached. The tab 115 is attached to the side extension.

Figure 12A:
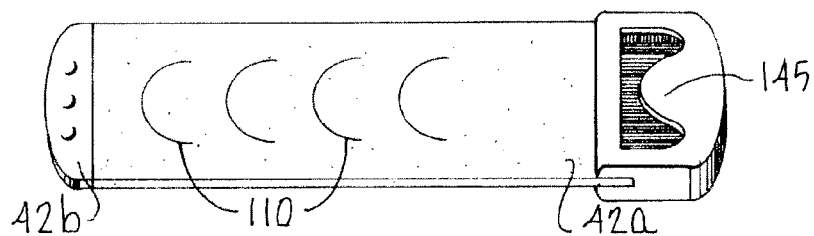
FIG. 12a is a perspective view of an embodiment of the fabric connector.
Figure 12B:
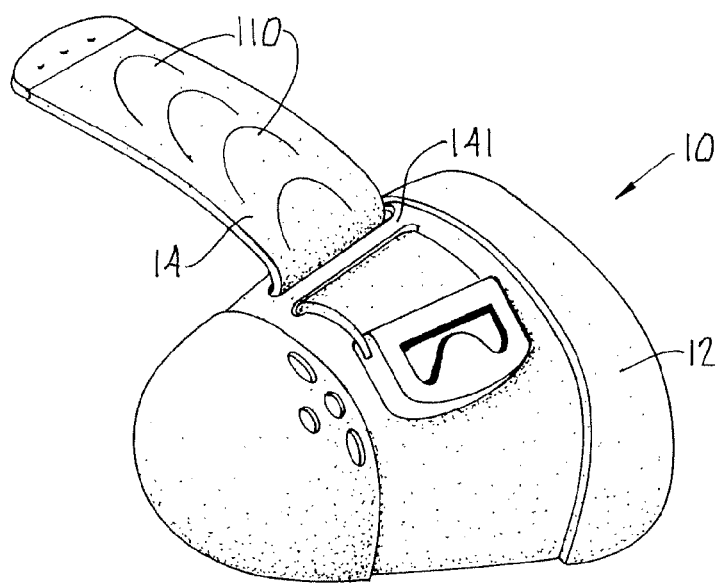
FIG. 12b is a perspective view of an embodiment of the site guard.

FIGS. 12a and 12b show an embodiment wherein in use, the plurality of holes 110 and the tab 145 are located on the fabric connector 14. The tab 145 is affixed to the inner portion 42a of the fabric connector 14. The hollow member 12 includes a bar 141. The fabric connector 14 passes under the bar 141, thereby attaching it to the hollow member 12. The bar 141 may be integral to the hollow member 12 or consist of a separate piece that is attached to the hollow member 12. Alternatively, fabric connector 14 may comprise a loop formed by connecting the inner portion 42a to the outer portion 42b after the fabric connector passes under bar 141.

The inner 42a and outer 42b portions may be connected in an overlapping or side-by-side manner.

Figure 13:
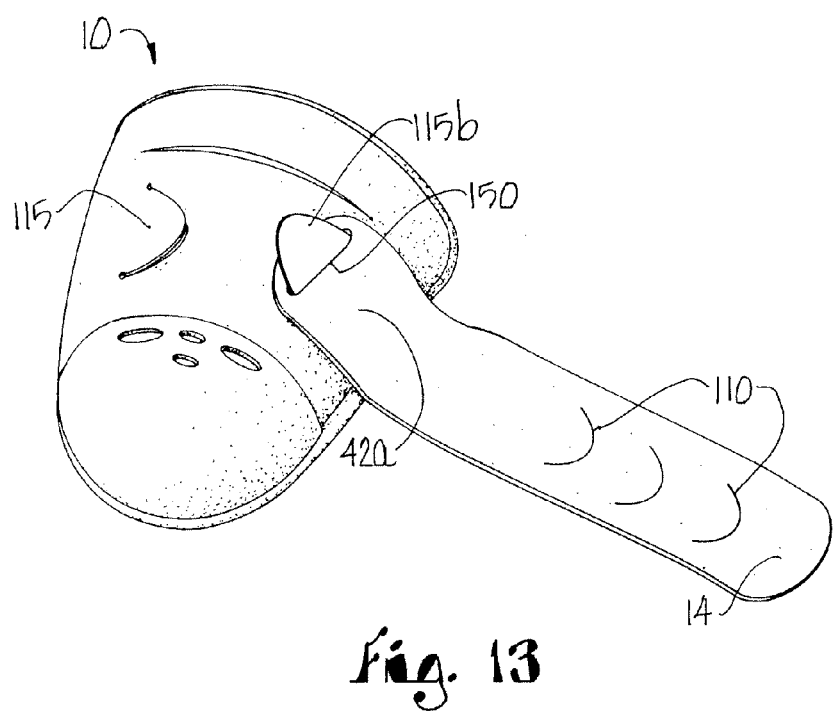
FIG. 13 is a perspective view of an embodiment of the site guard.

FIG. 13 shows an embodiment similar to the one shown in FIG. 9. In use, the fabric connector 14 includes a plurality of holes 110 that mate with a tab 115. The inner portion 42a of the fabric connector 14 includes a connector hole 150 that mates with a second a second tab 115b on the hollow member 12. In use, generally, the connector hole 150 is mated with the second tab 115b before one of the plurality of holes 110 mated with the first tab 115.

In any of the embodiments shown in FIGS. 9-13, the tab 115 can be, but is not limited to, an adhesive tab or a button tab. Alternatively, the tab 115 may be, but is not limited to, die cut or kiss cut from the element of the site guard 10 to which it is attached. Furthermore, the tab 115 can be of any size and shape that can mate with any of the holes 110.

Figure 14A:
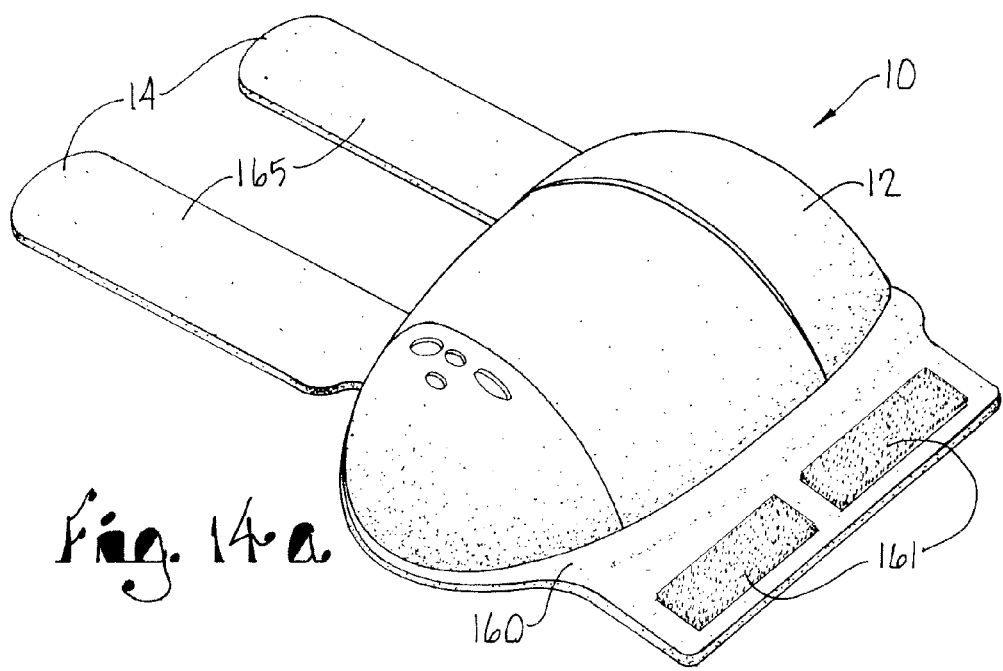
FIG. 14a is a perspective view of an embodiment of the site guard.
Figure 14B:
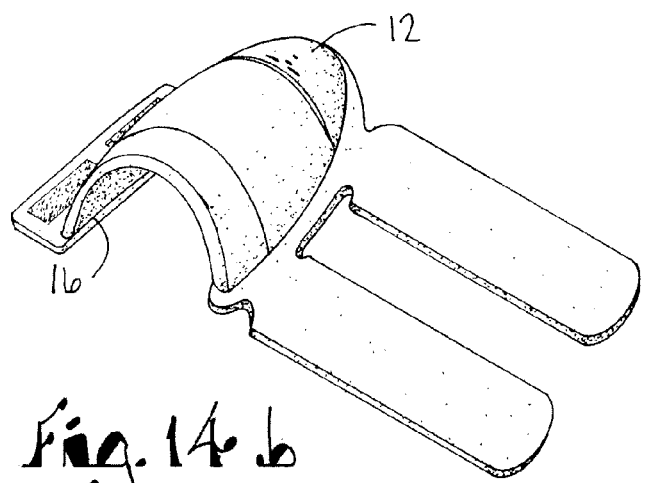
FIG. 14b is a perspective view of the embodiment of the site guard shown in FIG. 15 rotated 180 degrees.

In other embodiments (FIGS. 14-16), adhesive is used to affix the fabric connector 14 to the hollow member 12. In the embodiment shown in FIGS. 14a and 14b, the site guard 10 further includes a support 160. This support 160 is generally comprised of, but not limited to, a foam, such as a closed cell foam and may be manufactured by a molding process. The lower edge 16 of the hollow member 12 is attached to the support 160. Integrated with the support 160 is the fabric connector 14. In this embodiment, the fabric connector 14 is made from the same foam material as the support 160 and can comprise a plurality of minor strips 165. Furthermore, the support 160 includes at least one adhesive strip 161 or Velcro, or other closure means 20, which is generally equal in number the minor strips 165. In use, the fabric connector 14 (or minor strips 165) wrap around the desired body part and are affixed to the hollow member 12 using the adhesive strips 161, Velcro, or other closure means 20.

Figure 15:
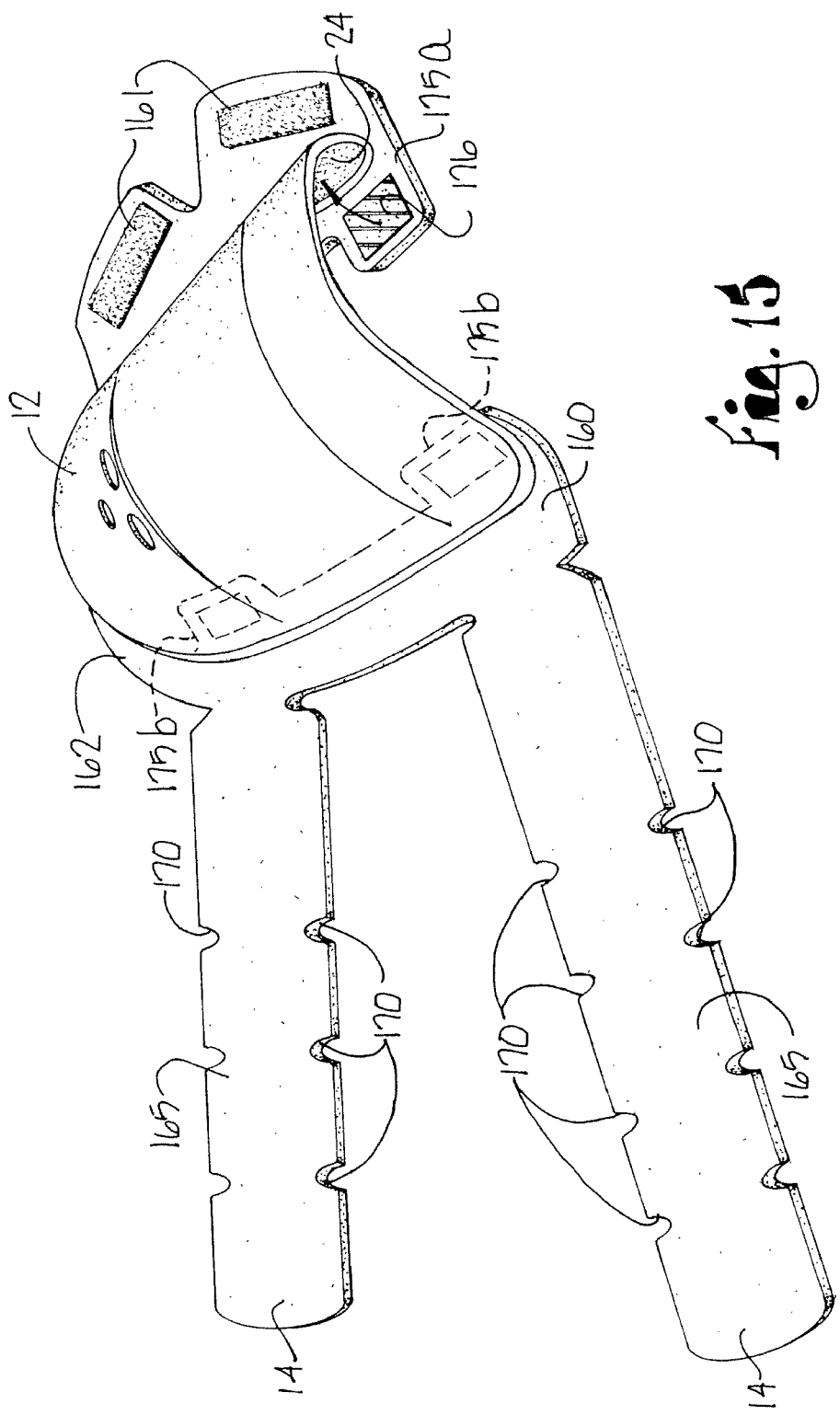
FIG. 15 is a perspective view of an embodiment of the site guard.

The embodiment shown in FIG. 15 also includes a support 160 with at least one adhesive strip 161, or other closure means 20, and a fabric connector 14. The fabric connector may comprise a plurality of minor strips 165. Additionally, the support 160 includes a base flange 162 and a plurality of base tabs 175a, 175b that each include adhesive pads 176, or other affixing means 23. The base flange 162 helps to spread the pressure from the hollow member 12 over a greater area, thus providing more comfort for the patient. The base tabs 175a, 175b, or other affixing means 23, are used to attach the hollow member 12 to the support 160. During assembly, the hollow member 12 is placed on the support 160. The support tabs 175 are bent upward to engage the inner dome 24 of the hollow member 12 wherein the adhesive pad 176 affixes the support tab 175 to the hollow member 12. Support tab 175a is shown as it would appear prior to being affixed to the hollow member 12, while support tabs 175b are shown after being affixed to hollow member 12. Additionally, the minor strips 165 each include a plurality of indentations 170 on one or both sides of the minor strips 165. These indentations 170 provide reference points for cutting, trimming or ripping the minor strips 165 down to the desired length to fit individual patients or body types. The support tabs 175a can be attached to hollow member 12 using adhesive, stitching, welding or any other affixing means 23.

Figure 16:
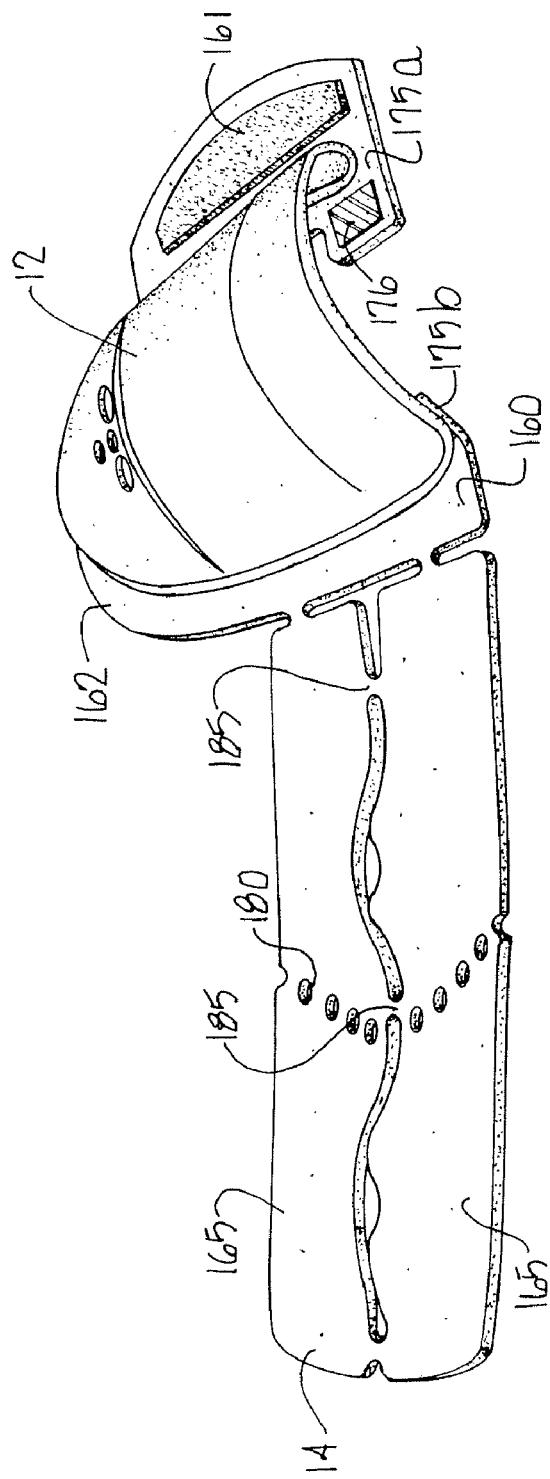
FIG. 16 is a perspective view of an embodiment of the site guard.

The embodiment shown in FIG. 16 shows an embodiment similar to the one shown in FIG. 15. It includes a support 160 which includes a support flange 162 and a plurality of support tabs 175a, 175b each including an adhesive pad 176. The support 160 is affixed to the hollow member 12 using the support tabs 175a, 175b as previously described. The support tabs 175a can be attached to hollow member 12 using adhesive, stitching, welding or any other means for affixing 23. This embodiment also includes an adhesive strip 161 (a plurality of adhesive strips may also be used), and a fabric connector 14. The fabric connector 14 comprises a plurality of perforations 180 (only one is shown here) located along its length. It further includes minor strips 165 intermittently connected together at connection points 185. This allows the minor strips 165 to be manufactured from a single piece of material. During use, the minor strips 165 can either be used connected together, or can be separated from each other at the connection points 185. Further, the minor strips 165 may be partially separated from each other to accommodate digits or other body parts. This allows greater flexibility when trying to attach the site guard 10 in the vicinity of a limb or joint and allows ambidextrous use on any sized patient on either hand, forearm, upper arm, leg, or other body part.

Figure 17A:
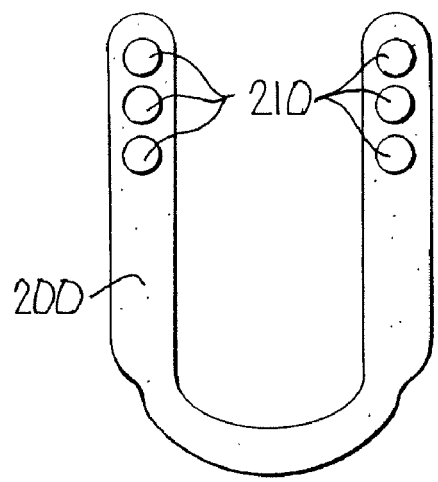
FIG. 17a is a top plan view of an embodiment of the utility strap.
Figure 17B:
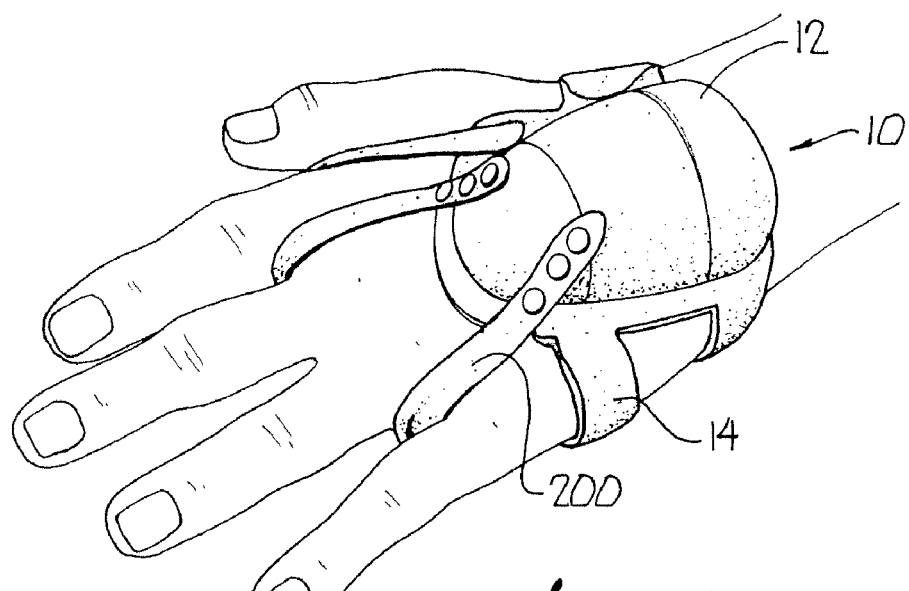
FIG. 17b is a perspective view of an embodiment of the site guard including the utility strap as used on a hand.

In another embodiment shown in FIGS. 17a and 17b, the fabric connector 14 can further comprise a utility strap 200. The utility strap 200 is a U-shaped strap that can be used to further secure the hollow member 12 to its desired location. It also includes at least one adhesive patch 210, or other affixing means 23, that is used to affix the utility strap 200 to the site guard 10. The utility strap 200 is particularly useful in securing the hollow member 12 to an irregularly shaped area or in the vicinity of a joint or appendage. FIG. 17b shows the utility strap 200 as it may be used to helps secure the hollow member 12 to the back of a hand. The utility strap 200 can be made from any of the same materials used for the fabric connector 14.

Figure 18:
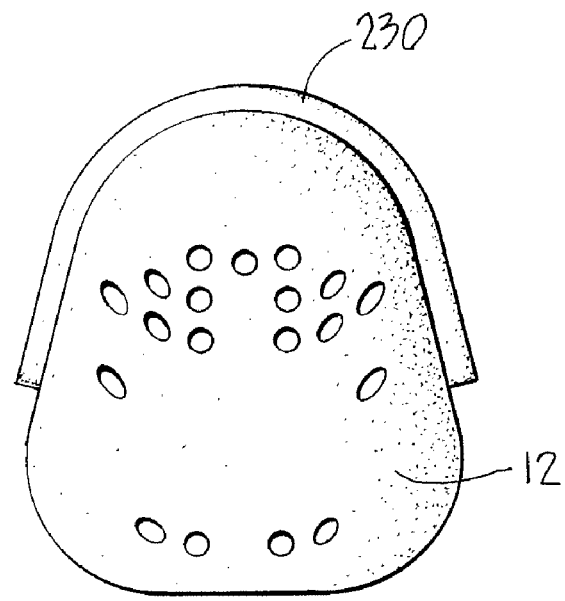
Figure 18:
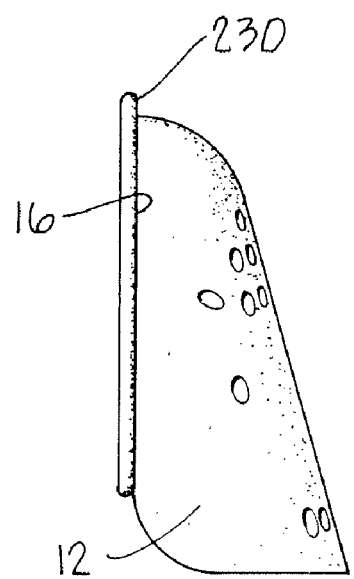

FIGS. 18a and 18b show an alternative embodiment of the hollow member 12. In this embodiment, the hollow member 12 comprises a member flange 230 attached to its lower edge 16. This member flange 230 helps distribute the pressure on the patient caused by the hollow member 12, thereby making the site guard more comfortable for the patient. The member flange 230 may be partially cushioned 27 or entirely cushioned 28 with the cushion 27, 28 taking any form and being of any material as described above, and particular in relation to FIG. 1c.

Figure 19:
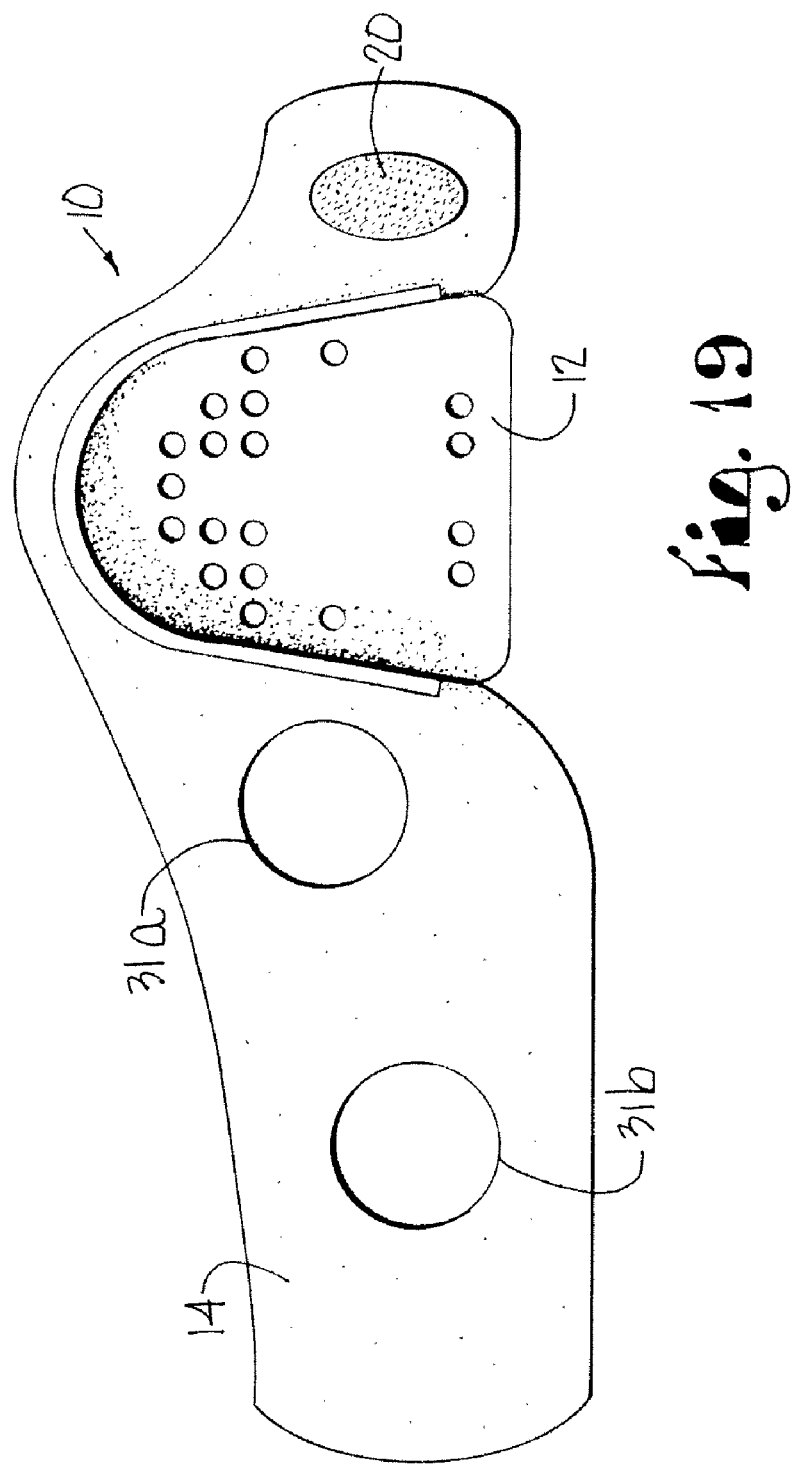
FIG. 19 is a top plan view of an embodiment of the site guard.

In an alternative embodiment depicted in FIG. 19, the fabric connector 14 comprises at least two openings 31 for ambidextrously accommodating one or more digits. The site guard 10 may include fabric connector 14 having a first and a second openings 31a and 31b, respectively, wherein the first opening 31a receives the right thumb and the second opening 31b receives the left thumb. Such an embodiment permits the use of one site guard 10 on either the left hand or the right hand, thereby foregoing the need to supply separate site guards 10 for each hand. The fabric connector 14 may be offset to one side of the hollow member 12 with both first and second openings 31a and 31b on the offset side as seen in FIG. 19 or may be centered with openings 31 in the fabric connector 14 on each side of the hollow member 12 as depicted in FIGS. 4a and 4c. Different sizes of the site guard 10 may accommodate different sizes of various body parts. As discussed above, any type of closure means 20 may secure the fabric connector 14 and the hollow member 12 to the patient.

Figure 22:
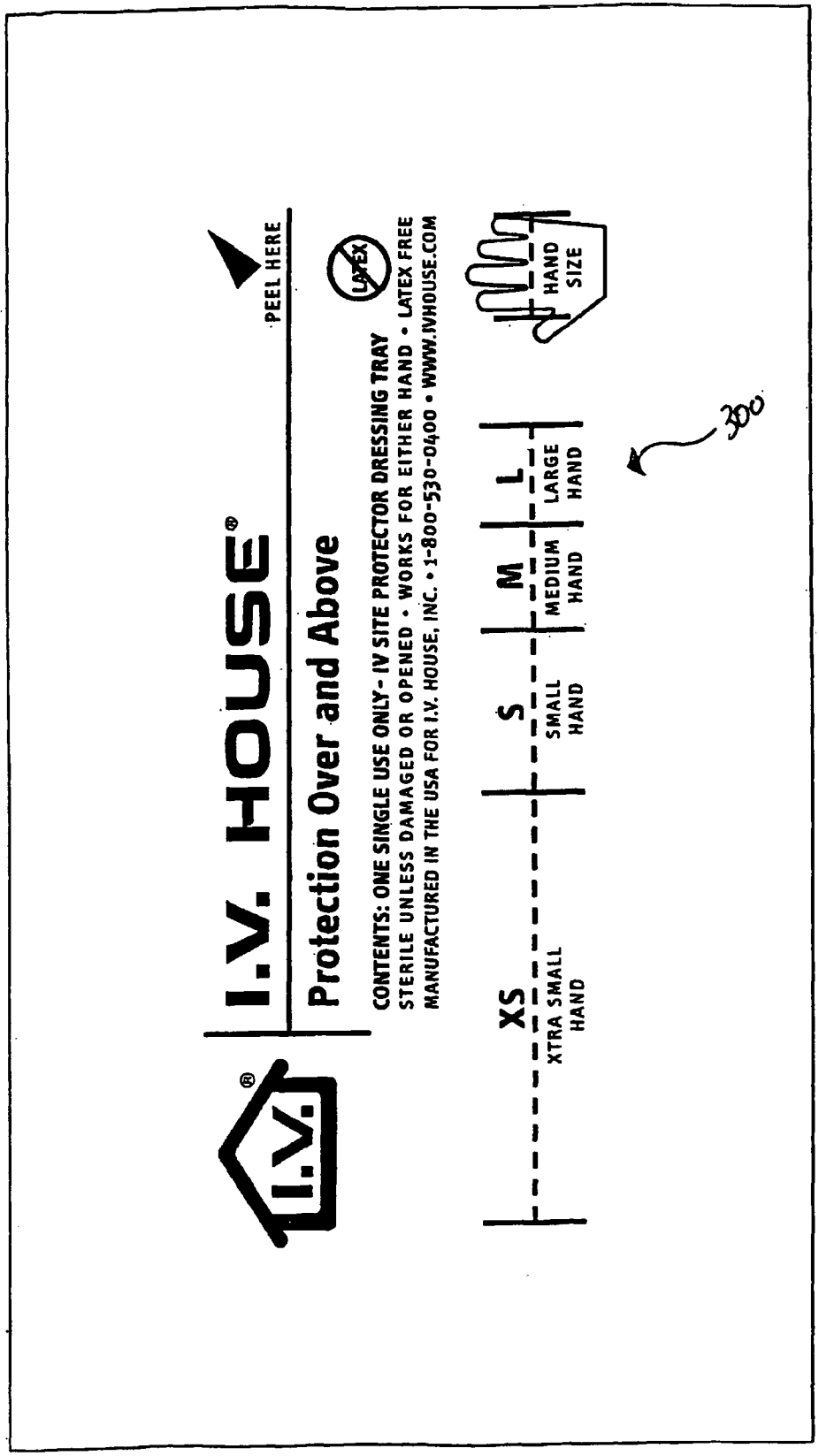
FIG. 22 is a plan view of an embodiment of the hand chart.

FIGS. 21a-e depict various sizes that may be utilized for the embodiment depicted in FIG. 19 and discussed herein. Sizes may include extra-small (XS), small (S), medium (M), large (L), and arm (for the wrist, forearm, or upperarm). Other sizes may also be included and may also accommodate other body parts. A hand chart 300 may be utilized to measure the patient's hand to determine the size to be used. FIG. 22 depicts the hand chart 300 including four sections: XS, S, M, and L. The hand chart 300 is used by placing the hand on the hand chart 300. In one embodiment, the width of the hand is measured from the index finger to the pinkie finger. A hand that is measured to approximately 3.125 inches or less falls in the extra small range; a hand that is measured between approximately 3.125 inches to approximately 4.25 inches falls in the small range; a hand that is measured between approximately 4.25 inches to approximately 5.0 inches falls in the medium range; and a hand that is measured between approximately 5.0 inches to approximately 5.75 inches falls in the large range. The skilled artisan will recognize that these ranges may vary with different types of site guards 10.

Figure 20:
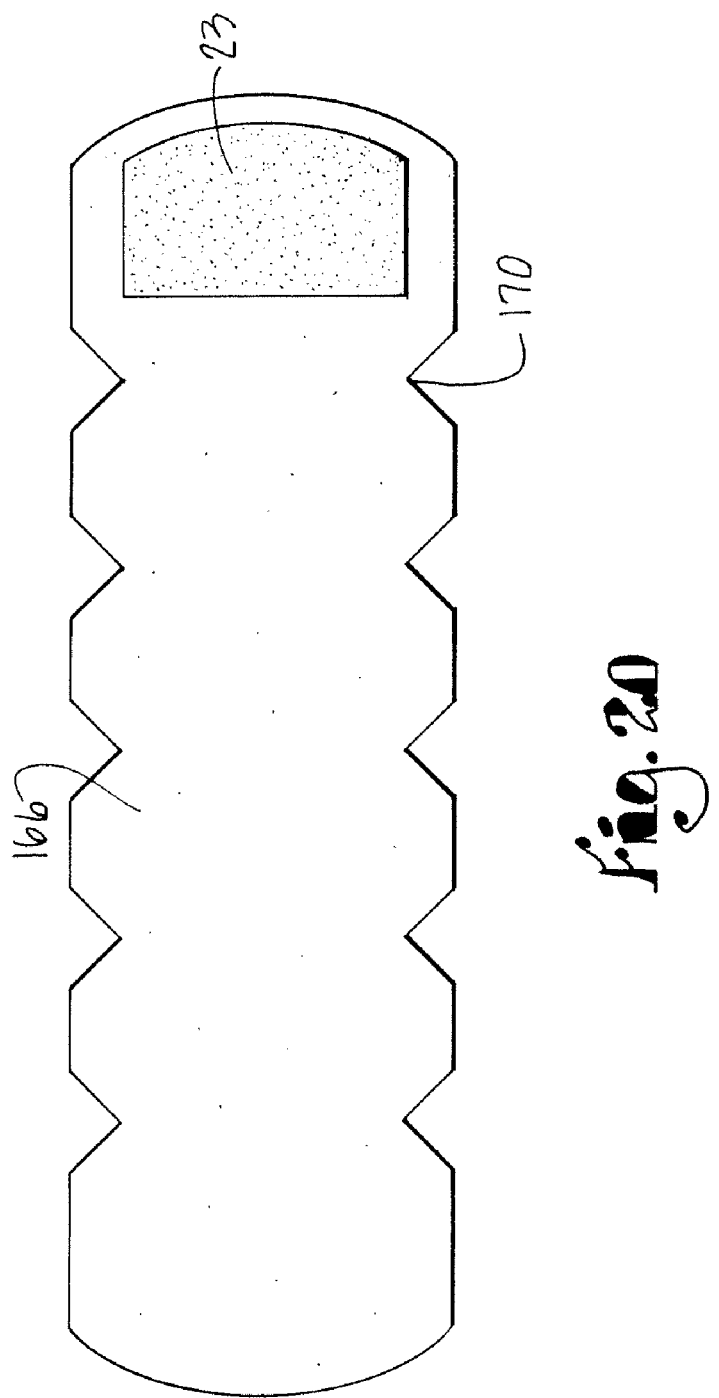
FIG. 20 is a top plan view of the extender for the fabric connector.
Figure 21A:
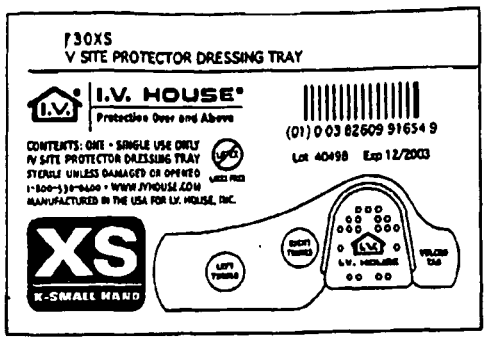
FIG. 21a is a plan view of an embodiment of a site guard.
Figure 21B:
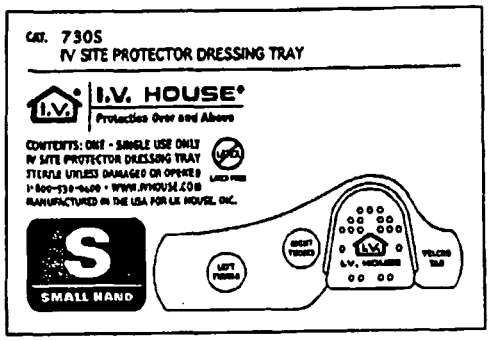
FIG. 21b is a plan view of an embodiment of a site guard.
Figure 21C:
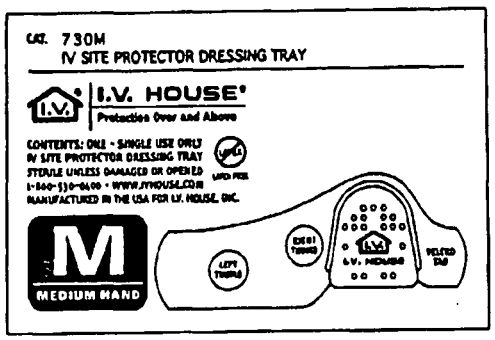
FIG. 21c is a plan view of an embodiment of a site guard.
Figure 21D:
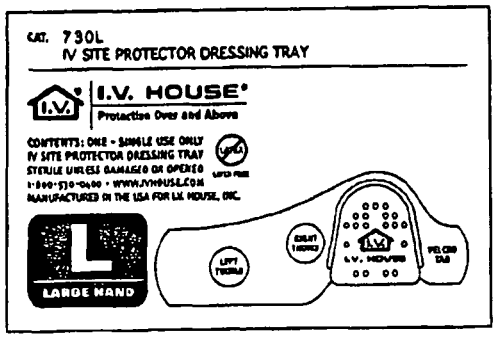
FIG. 21d is a plan view of an embodiment of a site guard.
Figure 21E:
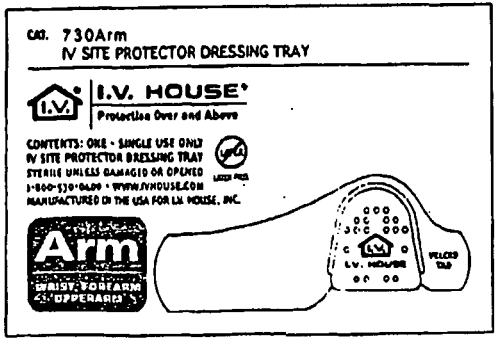
FIG. 21e is a plan view of an embodiment of a site guard.

In any of the embodiments described above, the fabric connector 14 may comprise an extender 166 shown in FIG. 20 to be used with large or obese patients or with a large body part. The extender 166 comprises any of the fabric connectors 14 described herein and provides an extension thereto and may be attached to the fabric connector 14 with affixing means 23 as described above. In one embodiment the extender 166 is 12 inches long with Velcro every two inches to affix to the patient at adjustable lengths. Perforations 180 or indentations 170 may be used to cut, rip or tear the extender 166 to fit individual patients or body types.

Although the invention has been described with respect to specific embodiments, it should be appreciated that other embodiments utilizing the concept of the present invention are possible without departing from the scope of the invention. The invention, for example, is not intended to be limited to the specific materials discussed and exemplified and disclosed in these embodiments; rather the invention is defined by the claims and the equivalents thereof.

What is claimed is:

1. A site guard, comprising:
   (a) a hollow member having a U-shaped base, the base having an edge to be positioned upon a patient adjacent a site, the base having a width sufficient to straddle the site and a length and a height sufficient to cover the site, the base joined to a sidewall to form a cover;
   (b) a member flange attached to the lower edge of the hollow member;
   (c) at least one fabric connector affixed to the member flange such that it does not traverse the sidewall, wherein, the fabric connector covers a whole surface of the member flange;
   (d) means for affixing the hollow member to the at least one fabric connector; and
   (e) means for closing the fabric connector on the patient.

2. The site guard as recited in claim 1, wherein the at least one fabric connector further comprises at least one opening to accommodate various body parts.

3. The site guard as recited in claim 2, wherein the at least one fabric connector comprises a first opening and a second opening configured to ambidextrously accommodate one or more digits.

4. The site guard as recited in claim 3, wherein the first opening is configured to receive the right thumb and the second opening is configured to receive the left thumb.

5. The site guard as recited in claim 1, wherein the at least one fabric connector comprises a material selected from the group consisting of tubular material, tubular mesh, stretch wrap, burn net, gauze, cotton cloths or blend, latex-free material, soft cloth, nylon, polymeric material, polypropylene material, polytetrahydrofluoroethylene (PTFE), transparent plastic material, hook-and-loop fastener strap, and combinations of any of the foregoing.

6. The site guard as recited in claim 5, wherein the tubular mesh comprises at least one opening to accommodate various body parts.

7. The site guard as recited in claim 6, wherein the tubular mesh comprises a plurality of openings to accommodate varying sizes of the various body parts.

8. The site guard as recited in claim 1, wherein the closure means comprises a first tab and a plurality of holes configured to receive the first tab.

9. The site guard as recited in claim 8, wherein the first tab is selected from the group consisting of an adhesive tab and a button tab.

10. The site guard as recited in claim 8, wherein the at least one fabric connector further comprises the plurality of holes.

11. The site guard as recited in claim 8, wherein the fabric connector further comprises the first tab.

12. The site guard as recited in claim 1, wherein the closure means comprises a support integrated with the at least one fabric connector.

13. The site guard as recited in claim 12, wherein the support comprises at least one adhesive strip configured to receive the at least one fabric connector.

14. The site guard as recited in claim 12, wherein the support further comprises the affixing means.

15. The site guard as recited in claim 1, wherein the fabric connector further comprises an agent.

16. The site guard as recited in claim 15, wherein the agent is selected from the group consisting of an antimicrobial, an antifungal, an antiviral, aloe, vitamin E, and combinations of any of the foregoing.

17. The site guard as recited in claim 1, wherein the hollow member further comprises at least one ventilation hole.

18. The site guard as recited in claim 17, comprising a plurality of ventilation holes.

19. The site guard as recited in claim 1, wherein the hollow member comprises the affixing means.

20. The site guard as recited in claim 1, wherein the hollow member and the at least one fabric connector comprise the affixing means, the affixing means of the hollow member configured to detachably couple to the affixing means of the at least one fabric connector.

21. The site guard as recited in claim 1, wherein the at least one fabric connector comprises a plurality of minor strips.

22. The site guard as recited in claim 1, wherein the at least one fabric connector comprises a plurality of indentations.

23. The site guard as recited in claim 1, wherein the at least one fabric connector comprises a plurality of perforations.

24. The site guard as recited in claim 1, wherein the at least one fabric connector comprises a plurality of connection points.

25. The site guard as recited in claim 1, wherein the at least one fabric connector comprises an extender.

26. The site guard as recited in claim 1, further comprising a cushion attached to the fabric connector opposite the lower edge of the hollow member.

27. The site guard as recited in claim 1, wherein the hollow member is fully closed.

28. The site guard as recited in claim 1, wherein the affixing means is selected from the group consisting of sewing, gluing, ultrasonic welding, chemical bonding, or using hook and loop fasteners or a pocket.

29. The site guard as recited in claim 1, wherein the closure means is selected from the group consisting of hook and loop fasteners, peel and stick tape, ties, pins, and clips.

30. The site guard as recited in claim 1, wherein the at least one fabric connector is bifurcated.

* * * * *